United States Patent
Bourbeau et al.

(10) Patent No.: US 10,889,579 B2
(45) Date of Patent: Jan. 12, 2021

(54) THIAZINE DERIVATIVES AS β-SECRETASE INHIBITORS AND METHODS OF USE

(71) Applicant: AMGEN INC., Thousand Oaks, CA (US)

(72) Inventors: Matthew P. Bourbeau, Woodland Hills, CA (US); Paul E. Harrington, Thousand Oaks, CA (US); Qingyian Liu, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 16/466,209

(22) PCT Filed: Dec. 13, 2017

(86) PCT No.: PCT/US2017/066179
§ 371 (c)(1),
(2) Date: Jun. 3, 2019

(87) PCT Pub. No.: WO2018/112083
PCT Pub. Date: Jun. 21, 2018

(65) Prior Publication Data
US 2020/0062743 A1 Feb. 27, 2020

Related U.S. Application Data

(60) Provisional application No. 62/434,714, filed on Dec. 15, 2016.

(51) Int. Cl.
*C07D 417/10* (2006.01)
*A61P 25/28* (2006.01)

(52) U.S. Cl.
CPC ............ *C07D 417/10* (2013.01); *A61P 25/28* (2018.01)

(58) Field of Classification Search
CPC .................................................... C07D 417/10
USPC ..................................................... 514/236.8
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| 5,942,400 A | 8/1999 | Anderson et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2011/0152253 A1 | 6/2011 | Motoki et al. |
| 2012/0238557 A1 | 9/2012 | Masui et al. |
| 2012/0245154 A1 | 9/2012 | Anan et al. |
| 2012/0245157 A1 | 9/2012 | Masui et al. |
| 2016/0046618 A1 | 2/2016 | Allen et al. |

FOREIGN PATENT DOCUMENTS

| | | |
|---|---|---|
| EP | 2 147 914 A1 | 1/2010 |
| EP | 2 151 435 A1 | 2/2010 |
| EP | 2 305 672 A1 | 4/2011 |
| EP | 2 703 401 A1 | 3/2014 |
| EP | 1 942 105 B1 | 4/2014 |
| WO | 2000/017369 A2 | 3/2000 |
| WO | 2009/134617 A1 | 11/2009 |
| WO | 2009/151098 A1 | 12/2009 |
| WO | 2010/013302 A1 | 2/2010 |
| WO | 2010/013794 A1 | 2/2010 |
| WO | 2011/005738 A1 | 1/2011 |
| WO | 2011/009898 A1 | 1/2011 |
| WO | 2011/029803 A1 | 3/2011 |
| WO | 2011/044181 A1 | 4/2011 |
| WO | 2011/069934 A1 | 6/2011 |
| WO | 2012/095463 A1 | 7/2012 |
| WO | 2012/095469 A1 | 7/2012 |
| WO | 2012/098213 A1 | 7/2012 |
| WO | 2012/098461 A1 | 7/2012 |
| WO | 2012/138734 A1 | 10/2012 |
| WO | 2012/139425 A1 | 10/2012 |
| WO | 2012/147762 A1 | 11/2012 |
| WO | 2012/156284 A1 | 11/2012 |
| WO | 2012/162330 A1 | 11/2012 |
| WO | 2012/162334 A1 | 11/2012 |

(Continued)

OTHER PUBLICATIONS

Alzforum Networking for A Cure, "Barcelona: Out of Left Field—Hit to The Eye Kills Bace Inhibitor," pp. 1-7 (Mar. 31, 2011); access online: www.alzforum.org/news/conference-coverage/barcelona-out-left-field-hit-eye-kills-bace-inhibitor (last accessed Dec. 16, 2015).

(Continued)

*Primary Examiner* — Kahsay Habte
(74) *Attorney, Agent, or Firm* — Markus Bergauer

(57) ABSTRACT

The present disclosure provides a class of compounds useful for the modulation of beta-secretase enzyme (BACE) activity. The compounds have a general Formula I:

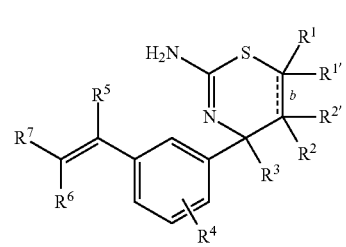

wherein variables $R^1$, $R^{1'}$, $R^2$, $R^{2'}$, $R^3$, $R^4$, $R^5$, $R^6$, $R^7$, and b of Formula I are defined herein. This disclosure also provides pharmaceutical compositions comprising the compounds, and uses of the compounds and compositions for treatment of disorders and/or conditions related to Aβ plaque formation and deposition, resulting from the biological activity of BACE. Such BACE mediated disorders include, for example, Alzheimer's Disease, cognitive deficits, cognitive impairments, and other central nervous system conditions.

20 Claims, No Drawings

(56) References Cited

FOREIGN PATENT DOCUMENTS

| | | |
|---|---|---|
| WO | 2013/004676 A1 | 1/2013 |
| WO | 2013/027188 A1 | 2/2013 |
| WO | 2013/028670 A1 | 2/2013 |
| WO | 2013/030713 A1 | 3/2013 |
| WO | 2013/142613 A1 | 9/2013 |
| WO | 2013/164730 A1 | 11/2013 |
| WO | 2013/182638 A1 | 12/2013 |
| WO | 2014/013076 A1 | 1/2014 |
| WO | 2014/045162 A1 | 3/2014 |
| WO | 2014/062549 A1 | 4/2014 |
| WO | 2014/062553 A1 | 4/2014 |
| WO | 2014/065434 A1 | 5/2014 |
| WO | 2014/066132 A1 | 5/2014 |
| WO | 2014/093190 A1 | 6/2014 |
| WO | 2014/097038 A1 | 6/2014 |
| WO | 2014/098831 A1 | 6/2014 |
| WO | 2014/099788 A9 | 6/2014 |
| WO | 2014/099794 A1 | 6/2014 |
| WO | 2014/138484 A1 | 9/2014 |
| WO | 2014/143579 A1 | 9/2014 |
| WO | 2016/022724 A1 | 2/2016 |
| WO | 2016/172255 A1 | 10/2016 |
| WO | 2017/024180 A1 | 2/2017 |
| WO | 2018/112081 A1 | 6/2018 |
| WO | 2018/112083 A1 | 6/2018 |
| WO | 2018/112084 A1 | 6/2018 |
| WO | 2018/112086 A1 | 6/2018 |
| WO | 2018/112904 A1 | 6/2018 |

OTHER PUBLICATIONS

Best, J. D. et al., "Quantitative Measurement of Changes in Amyloid-β(40) in the Rat Brain and Cerebrospinal Fluid Following Treatment with the γ-Secretase Inhibitor LY-411575 [N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide]," Journal of Pharmacology and Experimental Therapeutics 313(2):902-908 (2005).
Citron, M., "β-Secretase inhibition for the treatment of Alzheimer's disease—promise and challenge," TRENDS in Pharmacological Sciences 25(2):92-97 (2004).
Cole, S.L. and Vassar, R., "The Alzheimer's disease β-secretase enzyme, BACE1," Molecular Neurodegeneration 2(22):1-25 (2007).
De Meyer, G. et al., "Diagnosis-Independent Alzheimer Disease Biomarker Signature in Cognitively Normal Elderly People," Arch. Neurol. 67(8):949-956 (2010).
Dovey, H. F. et al., "Functional gamma-secretasae inhibitors reduce beta-amyloid peptide levels in brain," Journal of Neurochemistry 76:173-181 (2001).
Follo, C. et al., "Knock-Down of Cathepsin D Affects the Retinal Pigment Epithelium, Impairs Swim-Bladder Ontogenesis and Causes Premature Death in Zebrafish," PLoS One 6(7):e21908, pp. 1-13 (2011).
Games, D. et al., "Alzheimer-type neuropathology in transgenic mice overexpressing V717F β-amyloid precursor protein," Nature 373:523-527 (1995).
Götz, J. et al., "Transgenic animal models of Alzheimer's disease and related disorders: histopathology, behavior and therapy," Molecular Psychiatry 9:664-683 (2004).
Gulnik, S. V. et al., "Design of sensitive fluorogenic substrates for human cathepsin D," FEBS Lett. 413:379-384 (1997).
Harris, J. A. et al, "Transsynaptic Progression of Amyloid-β-Induced Neuronal Dysfunction within the Entorhinal-Hippocampal Network," Neuron 68:428-441 (2010).

Henley, D. B. et al., "Development of semagacestat (LY450139), a functional γ-secretase inhibitor, for the treatment of Alzheimer's disease," Expert Opin. Pharmacother. 10(10):1657-1664 (2009).
Hsia, A. Y. et al., "Plaque-independent disruption of neural circuits in Alzheimer's disease mouse models," Proc. Natl. Acad. Sci. USA 96:3228-3233 (1999).
Hsiao, K. et al., "Correlative Memory Deficits, Aβ Elevation, and Amyloid Plaques in Transgenic Mice," Science 274:99-102 (1996).
International Preliminary Report on Patentability and Written Opinion for International Patent Application No. PCT/US2017/066179, dated Jun. 18, 2019, pp. 1-6.
International Search Report for International Patent Application No. PCT/US2017/066179, dated Mar. 7, 2018, pp. 1-5.
Joachim, C. L. and Selkoe, D. J., "The Seminal Role of β-Amyloid in the Pathogenesis of Alzheimer Disease," Alzheimer Disease and Associated Disorders 6(1):7-34 (1992).
Koike, M. et al., "Involvement of two different cell death pathways in retinal atrophy of cathepsin D-deficient mice," Molecular and Cellular Neuroscience 22:146-161 (2003).
Luo, Y et al., "Mice deficient in BACE1, the Alzheimer's β-secretase, have normal phenotype and abolished β-amyloid generation," Nature Neuroscience 4:231-232 (2001).
Palop, J. J. and Mucke, L., "Amyloid-β-induced neuronal in Alzheimer's disease: from synapses toward neural networks," Nature Neuroscience 13(7):812-818 (2010).
Sabbagh, M. N. et al., "β-Amyloid and Treatment Opportunities for Alzheimer's Disease," Alzheimer's Disease Review 3:1-19 (1997).
Selkoe, D. J., "Soluble oligomers of the amyloid β-protein impair synaptic plasticity and behavior," Behavioural Brain Research 192:106-113 (2008).
Selkoe, D. J., "The Molecular Pathology of Alzheimer's Disease," Neuron 6:487-498 (1991).
Seubert, P. et al., "Isolation and quantification of soluble Alzheimer's β-peptide from biological fluids," Nature 359:325-327 (1992).
Shacka, J. J. and Roth, K. A., "Cathepsin D Deficiency and NCL/Batten Disease: There's More to Death than Apoptosis," Autophagy, 3(5):474-476 (2007).
Shankar, G. M. et al., "Amyloid-β protein dimers isolated directly from Alzheimer's brains impair synaptic plasticity and memory," Nature Medicine 14(8):837-842 (2008).
Siemers, E. R. et al., "Effects of a γ-secretase inhibitor in a randomized study of patients with Alzheimer's disease," Neurology 66:602-604 (2006).
Simers, E. R. et al., "Safety, Tolerability, and Effects on Plasma and Cerebrospinal Fluid Amyloid-β After Inhibition of γ-Secretase," Clin. Neuropharmacol. 30(6):317-325 (2007).
Sinha, S. et al., "Purification and cloning of amyloid precursor protein β-secretase from human brain," Nature 402:537-540 (1999).
Tanzi, R. E. and Bertram, L., "Twenty Years of the Alzheimer's Disease Amyloid Hypothesis: A Genetic Perspective," Cell 120(4):545-555 (2005).
Vassar, R. and Yan, R., "Targeting the β secretase BACE1 for Alzheimer's disease therapy," Lancet Neurology 13:319-329 (2014).
Walsh, D. M. and Selkoe, D. J., "Deciphering the Molecular Basis of Memory Failure in Alzheimer's Disease," Neuron 44(1):181-193 (2004).
Yasuda, Y. et al., "Characterization of New Fluorogenic Substrates for the Rapid and Sensitive Assay of Cathepsin E and Cathepsin D," J. Biochem. 125:1137-1143 (1999).
Yan R., "Stepping closer to treating Alzheimer's disease patients with BACE1 inhibitor drugs," Transl. Neurodegener. 5(13):1-11 (2016).
"A Study of CAD106 and CNP520 Versus Placebo in Participants at Risk for the Onset of Clinical Symptoms of Alzheimer's Disease (Generation S1)" https://clinicaltrials.gov/ct2/show/NCT02565511 (Nov 10, 2016—submitted date).

THIAZINE DERIVATIVES AS β-SECRETASE INHIBITORS AND METHODS OF USE

CROSS-REFERENCE TO RELATED APPLICATIONS

This application is a national stage application under 35 U.S.C. § 371 of International Application No. PCT/US2017/066179, having an international filing date of Dec. 13, 2017, which claims the benefit of U.S. Provisional Patent Application No. 62/434,714, filed Dec. 15, 2016, which is incorporated by reference herein in its entirety.

FIELD

The present disclosure relates generally to pharmaceutically active compounds and pharmaceutical compositions thereof for the modulation of beta site amyloid precursor protein cleaving enzyme (BACE) activity. Provided herein are uses of these compounds and pharmaceutical compositions thereof for treatment of disorders and/or conditions related to beta-amyloid plaque formation and deposition, resulting from the biological activity of BACE. Such BACE mediated disorders include, for example, Alzheimer's Disease, cognitive deficits, cognitive impairments, and other central nervous system conditions.

BACKGROUND

Alzheimer's disease (AD) affects greater than 12 million aging people worldwide, and, importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid (Aβ) peptide deposits in the brain (commonly referred to as Aβ "plaques" or "plaque deposits") and in cerebral blood vessels (beta amyloid angiopathy). A wealth of evidence suggests that Aβ and accompanying amyloid plaque formation is central to the pathophysiology of AD and is likely to play an early role in this intractable neurodegenerative disorder. Yan et al., *Lancet Neurol.* 13(3):319-329 (2014). The second change in AD is the formation of intraneuronal tangles, consisting of an aggregate form of the microtubule-binding protein tau. Besides being found in patients with AD, intraneuronal tangles are also found in other dementia-inducing disorders. Joachim et al., *Alzheimer. Dis. Assoc. Disord.* 6(1):7-34 (1992).

Several lines of evidence indicate that progressive cerebral deposition of Aβ peptide plays a seminal role in the pathogenesis of AD and can precede cognitive symptoms by years or even decades. Selkoe, *Neuron* 6(4):487-498 (1991). Release of Aβ peptide from neuronal cells grown in culture and the presence of Aβ peptide in cerebrospinal fluid (CSF) of both normal individuals and AD patients has been demonstrated. Seubert et al., *Nature* 359:325-327 (1992). Autopsies of AD patients have revealed large numbers of lesions comprising Aβ and tau peptides in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that Aβ peptide formation is a causative precursor or factor in the development of AD. More specifically, deposition of Aβ peptide in areas of the brain responsible for cognition is believed to be a major factor in the development of AD. Aβ plaques are primarily composed of Aβ peptide. Aβ peptide is derived from the proteolytic cleavage of a large transmembrane amyloid precursor protein (APP), and is a peptide comprised of about 39-42 amino acid residues. Aβ 1-42 (42 amino acids long) is thought to be the major component of these plaque deposits in the brains of AD patients. Citron, *Trends Pharmacol. Sci.* 25(2):92-97 (2004).

Similar plaques appear in some variants of Lewy body dementia and in inclusion body myositis, a muscle disease. Aβ peptides also form aggregates coating cerebral blood vessels in cerebral amyloid angiopathy. These plaques are composed of fibrillar Aβ aggregates that display a characteristic β-sheet structure, a protein fold shared by other peptides such as prions associated with protein misfolding diseases. Research on laboratory rats suggest that the dimeric, soluble form of the peptide is a causative agent in the development of AD and is the smallest synaptotoxic species of soluble amyloid beta oligomer. Shankar et al., *Nat. Med.* 14(8):837-842 (2008).

Several aspartyl proteases, including β-secretase and γ-secretase, are involved in the processing or cleavage of APP, resulting in the formation of Aβ peptide. β-Secretase (BACE, also commonly referred to as memapsin) is the first to cleave APP to generate two fragments: (1) a first N-terminus fragment (sAPPβ) and (2) a second C-99 fragment, which is subsequently cleaved by γ-secretase to generate the Aβ peptide. APP has also been found to be cleaved by α-secretase to produce sAPPα, a secreted form of APP that does not result in Aβ plaque formation. This alternate pathway precludes the formation of Aβ peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the β-secretase specific cleavage site. BACE is present in two forms, BACE 1 and BACE 2, designated as such depending upon the specific cleavage site of APP. β-Secretase is described in Sinha et al., *Nature* 402:537-540 (1999) and International Patent Application Publication No. WO2000/017369. It has been proposed that Aβ peptide accumulates as a result of APP processing initiated by BACE. Moreover, in vivo processing of APP at the β-secretase cleavage site is thought to be a rate-limiting step in Aβ peptide production. Sabbagh et al., *Alzheimer's Disease Review* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of Aβ peptide. BACE knockout mice do not produce Aβ peptide and are free from AD associated pathologies including neuronal loss and certain memory deficits. Cole et al., *Molecular Neurodegeneration* 2:22, pages 1-25 (2007). When crossed with transgenic mice that over express APP, the progeny of BACE deficient mice show reduced amounts of Aβ peptide in brain extracts as compared with control animals. Luo et al., *Nat. Neurosci.* 4(3):231-232 (2001). The fact that BACE initiates the formation of Aβ peptide, and the observation that BACE levels are elevated in this disease provide direct and compelling reasons to develop therapies directed at BACE inhibition, thus, reducing Aβ peptide formation and its associated toxicities. To this end, inhibition of β-secretase activity and a corresponding reduction of Aβ peptide in the brain should provide a therapeutic method for treating AD and other Aβ peptide or plaque related disorders.

Consequently, the approach of regulating or reducing Aβ peptide formation and deposition as a potential treatment for AD has received tremendous attention, support and commitment from both researchers and investors alike. A small molecule γ-secretase inhibitor, LY450139 ("Semagacestat"), an Aβ peptide lowering agent, advanced to phase III clinical trials for the treatment of AD. The pharmacokinetics of semagacestat in plasma, as well as the plasma and cerebral spinal fluid (CSF) Aβ peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (Henley et al., *Expert Opin. Pharmacother.* 10(10): 1657-1664 (2009); Siemers et al., *Clin. Neuropharmacol.* 30(6): 317-325 (2007); and Siemers et al., *Neurology* 66(4): 602-604 (2006)). Additional approaches have been taken in attempts to treat AD and plaque-related disorders. See, for example, Yan et al., *Lancet Neurology* 13(3):319-329 (2014).

Furthermore, each of the following exemplary patent application publications describes inhibitors of BACE, useful for treating AD and other β-secretase mediated disorders: WO2014/098831, WO2014/099794, WO2014/099788, WO2014/097038, WO2014/093190, WO2014/066132, WO2014/065434, WO2014/062553, WO2014/062549, WO2014/045162, WO2014/013076, WO2013/182638, WO2013/164730, WO2013/030713, WO2013/028670, WO2013/004676, WO2012/162334, WO2012/162330, WO2012/147762, WO2012/139425, WO2012/138734, US2012/0245157, US2012/0245154, US2012/0238557, WO2011/029803, WO2011/005738, US2011/0152253, WO2010/013794, WO2010/013302, US2010/0160290, US2010/0075957, WO2009/151098, WO2009/134617, US2009/0209755, US2009/0082560, EP2703401 (equivalent of WO2012/146762) and EP1942105.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein CatD has been implicated in undesirable side effects. For instance, the inhibition of CatD is believed to be linked to adverse retinal development and retinal atrophy. Particularly, in mice it was found that CatD is essential for the metabolic maintenance of retinal photoreceptor cells and that its deficiency induces apoptosis of the cells, while the loss of inner nuclear layer (INL) neurons is mediated by nitric oxide release from microglial cells. However, in the very same mice, it was also found that no atrophic change was detected in the retina of mice deficient in Cathepsin B or L. Koike et al., *Mol. Cell Neurosci.* 22(2):146-161 (2003). Further, animal models of CatD deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. Shacka et al., *Autophagy* 3(5):474-476 (2007). Finally, an adverse effect of the inhibition of CatD is evident from the data presented in Folio et al., *PLoS One* 6(7):e21908 (2011). The authors of the PLoS One paper found that knock-down of CatD affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyperpigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human BACE-mediated AD clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Phase I dosing trial was terminated and people brought in for eye assessments did not show any abnormalities. (Alzheimer's Research Forum News, 3-31-2011 reporting on Martin Citron's presentation at the AD/PD Conference 3-2011 in Barcelona, Spain).

Hence, it is desirable to provide compounds which modulate the activity of and are selective for BACE, while not suffering from undesirable side effects possibly due to intervention with or the reduction and/or direct or indirect inhibition of the expression and/or function of other proteins or biological pathways.

SUMMARY

The compounds disclosed herein are useful for the modulation of β-secretase activity, and as treatment of AD. Particularly, the compounds provided herein are useful for the regulation or reduction of the formation of Aβ peptide and, consequently, the regulation and/or reduction of formation of Aβ plaque both in the brain, as well as in the CNS. To this end, the compounds are useful for the treatment of AD and other β-secretase and/or plaque-related and/or mediated disorders. For example, the compounds are useful for the prophylaxis and/or treatment, acute and/or chronic, of AD and other diseases or conditions involving the deposition or accumulation of Aβ peptide, and formation of plaque, in the brain.

First, provided herein is a compound of Formula I

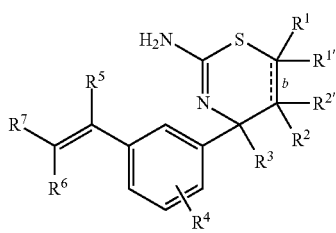

or a tautomer thereof, or a pharmaceutically acceptable salt of said compound or tautomer, wherein
$R^1$ and $R^{1'}$, independently, are H, $C_{1-6}$alkyl, —C(O)O$C_{1-6}$ alkyl, —C(O)NH$C_{1-6}$alkyl, or —C(O)-heterocycloalkyl, wherein the $C_{1-6}$alkyl and the $C_{1-6}$alkyl portions of —C(O)O$C_{1-6}$ alkyl and —C(O)NH$C_{1-6}$alkyl are optionally substituted with one to three fluoro substituents;
$R^2$ and $R^{2'}$ are H;
b is a single bond, if $R^1$, $R^{1'}$, $R^2$ and $R^{2'}$ are present;
b is a double bond, if one of $R^1$ and $R^{1'''}$ and one of $R^2$ and $R^{2'}$ is not present;
$R^3$ is $C_{1-4}$alkyl;
$R^4$ is halogen;
$R^5$ is H or F; and
one of $R^6$ and $R^7$ is F or H and the other of $R^6$ and $R^7$ is a 6-membered nitrogen-containing heteroaryl, which heteroaryl is optionally substituted with halogen, —CN, or 2-propynyloxy, wherein at least one of $R^5$, $R^6$, or $R^7$ is F.

Second, provided herein are pharmaceutical compositions comprising a compound of Formula I and a pharmaceutically acceptable excipient.

Third, provided herein are compounds of Formula I or pharmaceutical compositions thereof for use as a medicament.

Fourth, provided herein are compounds of Formula I or pharmaceutical compositions thereof for use in reducing beta amyloid peptide levels in the cerebral spinal fluid of a subject.

Fifth, provided herein are compounds of Formula I or pharmaceutical compositions thereof for use in treating Alzheimer's disease, cognitive impairment, or a combination thereof in a subject. In addition, provided herein are compounds of Formula I or pharmaceutical compositions thereof for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Sixth, provided herein are compounds of Formula I or pharmaceutical compositions thereof for use in reducing formation of plaque in the brain of a subject.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

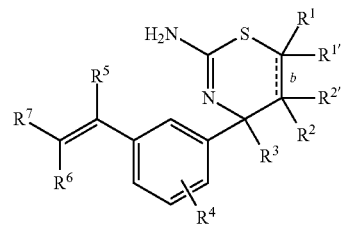

or a tautomer thereof, or a pharmaceutically acceptable salt of said compound or tautomer, wherein
$R^1$ and $R^{1'}$, independently, are H, $C_{1-6}$alkyl, —C(O)O$C_{1-6}$ alkyl, —C(O)NH$C_{1-6}$alkyl, or —C(O)-heterocycloalkyl, wherein the $C_{1-6}$alkyl and the $C_{1-6}$alkyl portions of —C(O)O$C_{1-6}$ alkyl and —C(O)NH$C_{1-6}$alkyl are optionally substituted with one to three fluoro substituents;
$R^2$ and $R^{2'}$ are H;
b is a single bond, if $R^1$, $R^{1'}$, $R^2$ and $R^{2'}$ are present;
b is a double bond, if one of $R^1$ and $R^{1'}$ and one of $R^2$ and $R^{2'}$ is not present;
$R^3$ is $C_{1-4}$alkyl;
$R^4$ is halogen;
$R^5$ is H or F; and
one of $R^6$ and $R^7$ is F or H and the other of $R^6$ and $R^7$ is a 6-membered nitrogen-containing heteroaryl, which heteroaryl is optionally substituted with halogen, —CN, or 2-propynyloxy, wherein at least one of $R^5$, $R^6$, or $R^7$ is F.

Provided herein as an alternative Embodiment 1 is a compound of Formula I

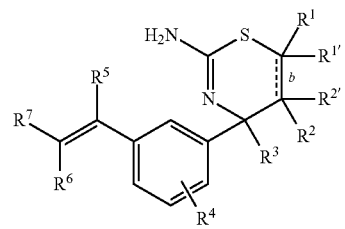

or a tautomer thereof, or a pharmaceutically acceptable salt of said compound or tautomer, wherein
$R^1$ and $R^{1'}$, independently, are H, $C_{1-6}$alkyl, —C(O)O$C_{1-6}$ alkyl, —C(O)NH$C_{1-6}$alkyl, or —C(O)-heterocycloalkyl, wherein the $C_{1-6}$alkyl and the $C_{1-6}$alkyl portions of —C(O)O$C_{1-6}$ alkyl and —C(O)NH$C_{1-6}$alkyl are optionally substituted with one to three fluoro substituents;
$R^2$ and $R^{2'}$ are H;

b is a single bond, if $R^1$, $R^{1'}$, $R^2$ and $R^{2'}$ are present;
b is a double bond, if one of $R^1$ and $R^{1'}$ and one of $R^2$ and $R^{2'}$ is not present;
$R^3$ is $C_{1-4}$alkyl;
$R^4$ is halogen;
$R^5$ is H or F; and
one of $R^6$ and $R^7$ is F or H and the other of $R^6$ and $R^7$ is a 6-membered nitrogen-containing heteroaryl, which heteroaryl is optionally substituted with —CN, or 2-propynyloxy, wherein at least one of $R^5$, $R^6$, or $R^7$ is F.

Provided herein as Embodiment 2 is the compound according to Embodiment 1, or a tautomer thereof, or a pharmaceutically acceptable salt of said compound or tautomer, wherein the compound of Formula I is a compound of Formula II

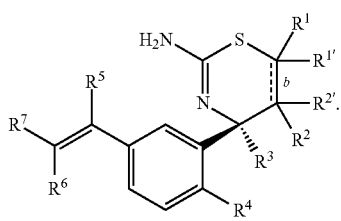

Provided herein as Embodiment 3 is the compound according to Embodiment 1, or a tautomer thereof, or a pharmaceutically acceptable salt of said compound or tautomer, wherein the compound of Formula I is a compound of Formula IIIA

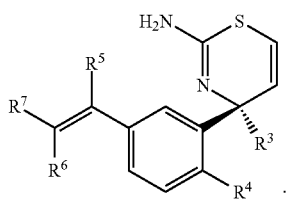

Provided herein as Embodiment 4 is the compound according to Embodiment 1, or a tautomer thereof, or a pharmaceutically acceptable salt of said compound or tautomer, wherein the compound of Formula I is a compound of Formula IIIB

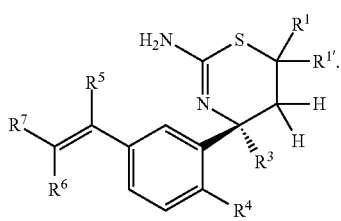

Provided herein as Embodiment 5 is the compound according to any one of Embodiments 1, 2, and 4, or a tautomer thereof, or a pharmaceutically acceptable salt of said compound or tautomer, wherein $R^1$ is H,

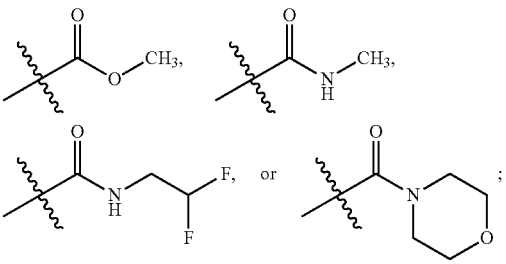

and
$R^{1'}$ is H or methyl.

Provided herein as Embodiment 6 is the compound according to any one of Embodiments 1, 2, 4, and 5, or a tautomer thereof, or a pharmaceutically acceptable salt of said compound or tautomer, wherein $R^{1'}$ is methyl.

Provided herein as Embodiment 7 is the compound according to any one of Embodiments 1-6, or a tautomer thereof, or a pharmaceutically acceptable salt of said compound or tautomer, wherein $R^3$ is methyl.

Provided herein as Embodiment 8 is the compound according to any one of Embodiments 1-7, or a tautomer thereof, or a pharmaceutically acceptable salt of said compound or tautomer, wherein $R^4$ is F.

Provided herein as Embodiment 9 is the compound according to any one of Embodiments 1-8, or a tautomer thereof, or a pharmaceutically acceptable salt of said compound or tautomer, wherein $R^6$ and $R^7$ is F or H and the other of $R^6$ and $R^7$ is pyridyl or pyrazinyl, which pyridyl or pyrazinyl is optionally substituted with Cl, —CN, or 2-propynyloxy.

Provided herein as Embodiment 10 is the compound according to any one of Embodiments 1-8, or a tautomer thereof, or a pharmaceutically acceptable salt of said compound or tautomer, wherein $R^6$ and $R^7$ is F or H and the other of $R^6$ and $R^7$ is pyridyl or pyrazinyl, which pyridyl or pyrazinyl is optionally substituted with —CN or 2-propynyloxy.

Provided herein as Embodiment 11 is the compound according to any one of Embodiments 1-9, or a tautomer thereof, or a pharmaceutically acceptable salt of said compound or tautomer, wherein one of $R^6$ and $R^7$ is

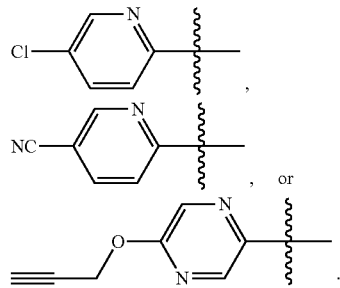

Provided herein as Embodiment 12 is the compound according to any one of Embodiments 1-10, or a tautomer thereof, or a pharmaceutically acceptable salt of said compound or tautomer, wherein one of $R^6$ and $R^7$ is

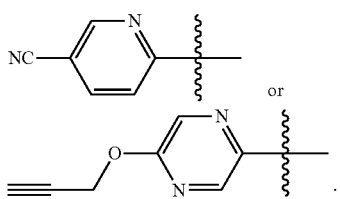

Provided herein as Embodiment 13 is the compound according to any one of Embodiments 1-12, or a tautomer thereof, or a pharmaceutically acceptable salt of said compound or tautomer, wherein
$R^5$ is F; and
$R^6$ is H.

Provided herein as Embodiment 14 is the compound according to any one of Embodiments 1-12, or a tautomer thereof, or a pharmaceutically acceptable salt of said compound or tautomer, wherein
$R^5$ is F; and
$R^7$ is H.

Provided herein as Embodiment 15 is the compound according to any one of Embodiments 1-12, or a tautomer thereof, or a pharmaceutically acceptable salt of said compound or tautomer, wherein
$R^5$ is H; and
$R^6$ is F.

Provided herein as Embodiment 16 is the compound according to any one of Embodiments 1-12, or a tautomer thereof, or a pharmaceutically acceptable salt of said compound or tautomer, wherein
$R^5$ is H; and
$R^7$ is F.

Provided herein as Embodiment 17 is the compound of Embodiment 1, or a tautomer thereof, or a pharmaceutically acceptable salt of said compound or tautomer, selected from
(S,Z)-4-(5-(2-(5-chloropyridin-2-yl)-2-fluorovinyl)-2-fluorophenyl)-4-methyl-4H-1,3-thiazin-2-amine;
(S,Z)-6-(2-(3-(2-amino-4-methyl-4H-1,3-thiazin-4-yl)-4-fluorophenyl)-1-fluorovinyl)nicotinonitrile;
(S,Z)-4-(5-(2-(5-chloropyridin-2-yl)-2-fluorovinyl)-2-fluorophenyl)-4-methyl-5,6-dihydro-4H-1,3-thiazin-2-amine;
(S,Z)-6-(2-(3-(2-amino-4-methyl-5,6-dihydro-4H-1,3-thiazin-4-yl)-4-fluorophenyl)-1-fluorovinyl)nicotinonitrile;
(4S,6R)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate;
(4S,6S)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate;
(4S,6S)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate;
(4S,6R)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate;
(4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
(4S,6S)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
6-((Z)-2-(3-((4S,6S)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
(4S,6R)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
(4S,6S)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
((4S,6S)-2-amino-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazin-6-yl)(morpholino)methanone;
(4S,6S)-2-amino-N-(2,2-difluoroethyl)-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazine-6-carboxamide; or
(4S,6S)-2-amino-4-(5-((Z)-2-(5-cyanopyridin-2-yl)-2-fluorovinyl)-2-fluorophenyl)-N,4,6-trimethyl-5,6-dihydro-4H-1,3-thiazine-6-carboxamide.

Provided herein as Embodiment 18 is the compound of Embodiment 1, or a tautomer thereof, or a pharmaceutically acceptable salt of said compound or tautomer, selected from
(S,Z)-6-(2-(3-(2-amino-4-methyl-4H-1,3-thiazin-4-yl)-4-fluorophenyl)-1-fluorovinyl)nicotinonitrile;
(S,Z)-6-(2-(3-(2-amino-4-methyl-5,6-dihydro-4H-1,3-thiazin-4-yl)-4-fluorophenyl)-1-fluorovinyl)nicotinonitrile;
(4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
(4S,6S)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
6-((Z)-2-(3-((4S,6S)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
(4S,6R)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
(4S,6S)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
((4S,6S)-2-amino-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazin-6-yl)(morpholino)methanone;
(4S,6S)-2-amino-N-(2,2-difluoroethyl)-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazine-6-carboxamide; or
(4S,6S)-2-amino-4-(5-((Z)-2-(5-cyanopyridin-2-yl)-2-fluorovinyl)-2-fluorophenyl)-N,4,6-trimethyl-5,6-dihydro-4H-1,3-thiazine-6-carboxamide.

Provided herein as Embodiment 19 is a pharmaceutical composition comprising the compound according to any of Embodiments 1-18, or a tautomer thereof, or a pharmaceutically acceptable salt of said compound or tautomer, and a pharmaceutically acceptable excipient.

Provided herein as Embodiment 20 is a compound according to any one of Embodiments 1-18, or a tautomer thereof, or a pharmaceutically acceptable salt of said compound or tautomer, or the pharmaceutical composition according to Embodiment 19 for use as a medicament.

Provided herein as Embodiment 21 is a compound according to any one of Embodiments 1-18, or a tautomer thereof, or a pharmaceutically acceptable salt of said compound or tautomer, or the pharmaceutical composition according to Embodiment 19 for use in reducing beta amyloid peptide levels in the cerebral spinal fluid of a subject.

Provided herein as Embodiment 22 is a compound according to any one of Embodiments 1-18, or a tautomer thereof, or a pharmaceutically acceptable salt of said compound or tautomer, or the pharmaceutical composition according to Embodiment 19 for use in treating Alzheimer's disease, cognitive impairment, or a combination thereof in a subject.

Provided herein as Embodiment 23 is a compound according to any one of Embodiments 1-18, or a tautomer thereof, or a pharmaceutically acceptable salt of said compound or tautomer, or the pharmaceutical composition according to Embodiment 19 for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 24 is a compound according to any one of Embodiments 1-18, or a tautomer thereof, or a pharmaceutically acceptable salt of said compound or tautomer, or the pharmaceutical composition according to Embodiment 19 for reducing formation of plaque in the brain of a subject.

Provided herein as Embodiment 25 is a use of the compound according to any one of Embodiments 1-18, or a tautomer thereof, or a pharmaceutically acceptable salt of said compound or tautomer, or the pharmaceutical composition according to Embodiment 19 in the preparation of a medicament for reducing beta amyloid peptide levels in the cerebral spinal fluid of a subject.

Provided herein as Embodiment 26 is a use of the compound according to any one of Embodiments 1-18, or a tautomer thereof, or a pharmaceutically acceptable salt of said compound or tautomer, or the pharmaceutical composition according to Embodiment 19 in the preparation of a medicament for treating Alzheimer's disease, cognitive impairment, or a combination thereof in a subject.

Provided herein as Embodiment 27 is a use of the compound according to any one of Embodiments 1-18, or a tautomer thereof, or a pharmaceutically acceptable salt of said compound or tautomer, or the pharmaceutical composition according to Embodiment 19 in the preparation of a medicament for the treatment of a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 28 is a use of the compound according to any one of Embodiments 1-18, or a tautomer thereof, or a pharmaceutically acceptable salt of said compound or tautomer, or the pharmaceutical composition according to Embodiment 19 in the preparation of a medicament for the reduction of formation of plaque in the brain of a subject.

Provided herein as Embodiment 29 is a method of reducing beta amyloid peptide levels in the cerebral spinal fluid of a subject in need thereof, the method comprising administering to the subject a therapeutically effective amount of the compound according to any one of Embodiments 1-18, or a tautomer thereof, or a pharmaceutically acceptable salt of said compound or tautomer.

Provided herein as Embodiment 30 is a method of treating Alzheimer's disease, cognitive impairment or a combination thereof in a subject in need thereof, the method comprising administering to the subject a therapeutically effective amount of the compound according to any one of Embodiments 1-18, or a tautomer thereof, or a pharmaceutically acceptable salt of said compound or tautomer.

Provided herein as Embodiment 31 is a method of treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject in need thereof, the method comprising administering to the subject a therapeutically effective amount of the compound according to any one of Embodiments 1-18, or a tautomer thereof, or a pharmaceutically acceptable salt of said compound or tautomer.

Provided herein as Embodiment 32 is a method of reducing the formation of plaque in the brain of a subject in need thereof, the method comprising administering to the subject a therapeutically effective amount of the compound according to any one of Embodiments 1-18, or a tautomer thereof, or a pharmaceutically acceptable salt of said compound or tautomer.

If an alternative embodiment to a certain embodiment is provided, a reference to the certain embodiment is also considered to be a reference to the alternative of said certain embodiment provided, if appropriate. For example, the reference in Embodiment 32 to, inter alfa, Embodiment 1 is meant to also include a reference to the alternative Embodiment 1 provided hereinabove.

The foregoing merely summarizes certain aspects of this disclosure and is not intended, nor should it be construed, as limiting the disclosure in any way.

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more assymetric carbon atoms, and bonds with a hindered rotation, and therefore, may exist as stereoisomers, such as double-bond isomers (i.e., geometric isomers (E/Z)), enantiomers, diastereomers, or atropoisomers. Accordingly, the scope of the instant disclosure is to be understood to encompass all possible stereoisomers of the illustrated compounds including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers) of any chemical structures disclosed herein (in whole or in part). This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, Ind., 1972).

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I:

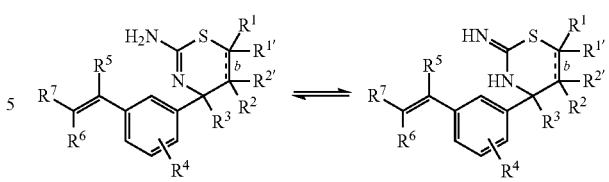

Accordingly, the scope of the instant disclosure is to be understood to encompass all tautomeric forms of the compounds disclosed herein.

Isotopically-Labelled Compounds

Further, the scope of present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I, for example, those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with isotopes such as deuterium ($^2$H) may afford certain therapeutic advantages resulting from greater metabolic stability, for example, increased in vivo half-life or reduced dosage requirements, and hence may be advantageous in some circumstances. Substitution with positron emitting isotopes, such as $^{11}$C, $^{18}$F, $^{15}$O and $^{13}$N, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagents in place of the non-labelled reagent previously employed.

Solvates

As discussed above, the compounds disclosed herein and the stereoisomers, tautomers and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Amorphous and Crystalline Forms

In certain embodiments, the compounds described herein and the stereoisomers, tautomers, isotopically-labelled forms thereof or pharmaceutically acceptable salts of any of the foregoing or solvates of any of the foregoing may exist in different forms, such as amorphous forms and crystalline forms (polymorphs). Accordingly, the scope of the instant disclosure is to be understood to encompass all such forms.

Miscellaneous Definitions

This section will define additional terms used to describe the scope of the compounds, compositions and uses disclosed herein.

The term "$C_{x-y}$alkyl" as used herein refers to a straight or branched chain hydrocarbon containing from x to y carbon atoms, for example, 1 to 4 and 1 to 6 carbon atoms. Representative examples of $C_{1-4}$ alkyl include, but are not limited to, methyl, ethyl, n-propyl, iso-propyl, n-butyl, sec-butyl, iso-butyl, and tert-butyl. Representative examples of $C_{1-6}$ alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" as used herein refers to a carbocyclic substituent obtained by removing hydrogen from a saturated carbocyclic molecule wherein the cyclic framework has 3 to 8 carbons. A "cycloalkyl" may be a monocyclic ring, examples of which include cyclopropyl, cyclobutyl, cyclopentyl, cyclohexyl, cycloheptyl, and cyclooctyl.

The term "halogen" as used herein refers to —F, —Cl, —Br, or —I.

The term "6-membered nitrogen-containing heteroaryl" as used herein refers to a heteroaryl ring having 6 ring atoms selected from carbon or nitrogen, wherein one to four of the ring atoms are nitrogen. Examples of 6-membered nitrogen-containing heteroaryls include, but are not limited to, pyridyl, pyrazinyl, pyrimidinyl, and pyridazinyl.

The term "heterocycloalkyl" as used herein refers to a cycloalkyl as defined above, wherein at least one of the ring carbon atoms is replaced with a heteroatom selected from nitrogen, oxygen or sulfur. Examples of six membered heterocycloalkyl include, but are not limited to, piperidine, piperazine, and morpholine.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, 2$^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "treating" as used herein refers not only to treating a subject to relieve the subject of one or more signs and symptoms of a disease or condition or to eliminate one or more such signs and symptoms, but also to prophylactically treating an asymptomatic subject to prevent the onset of the disease or condition or preventing, slowing or reversing the progression of the disease or condition.

The term "therapeutically effective amount" as used herein refers to that amount of a compound disclosed herein that will elicit the biological or medical response of a tissue, a system, or subject that is being sought by a researcher, veterinarian, medical doctor or other clinician. The term also encompasses the amount of compound disclosed herein that will prevent or reduce the risk of occurrence of the biological or medical event that is sought to be prevented in a tissue, a system, or subject by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following schemes are the variables as defined for Formula I, unless otherwise noted. All starting materials are either commercially available, for example, from Sigma-Aldrich Chemical Company, Inc., St. Louis, Mo., USA, or known in the art and may be synthesized by employing known procedures using ordinary skill. Starting material may also be synthesized via the procedures disclosed herein.

Scheme 1

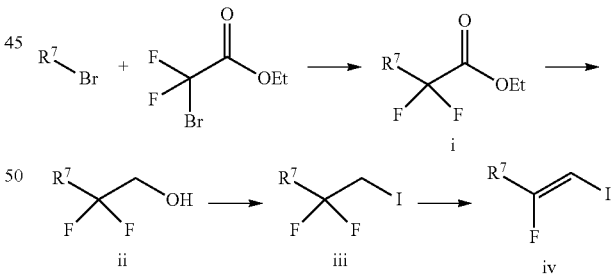

The alkene iv may be synthesized as shown in Scheme 1. The starting material $R^7$—Br is reacted with ethyl 2-bromo-2,2-difluoroacetate to give ester i. Ester i is then reduced, for example, with sodium borohydride, to give alcohol ii. The OH group of alcohol ii is then transformed into an iodo group yielding compound iii by transforming the OH group in a leaving group followed by a nucleophilic substitution, for example, by reacting alcohol ii with triflic anhydride in presence of a base, such as pyridine, followed by reaction with I$^-$, sourced from, for example, sodium iodide. Alkene iv is then obtained by reacting compound iii with a base, such as potassium tert-butoxide.

Scheme 2

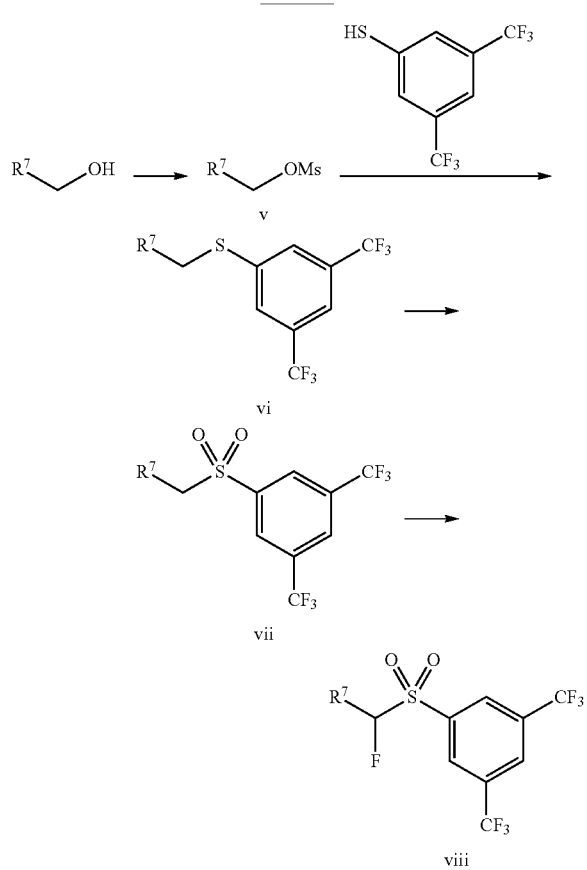

Sulfone viii may be synthesized as shown in Scheme 2. First, the OH group of R⁷CH₂OH is transformed into a leaving group, for example by reacting R⁷CH₂OH with methane sulfonyl chloride in presence of a base, such as trimethylamine, to give compound v. Then, compound v is reacted with 3,5-bis(trifluoromethyl)benzenethiol in presence of a base, such as sodium hydroxide, to give compound vi. Alternatively, R⁷CH₂X, wherein X is Cl, Br, or I, may be directly reacted with 3,5-bis(trifluoromethyl)benzenethiol in presence of a base, such as potassium carbonate, to give compound vi. The sulfone vii is obtained by reacting compound vi under oxidizing conditions using, for example, hydrogen peroxide. Sulfone viii was obtained reacting sulfone vii with an electrophilic fluorination agent, such as N-fluorodibenzenesulfonimide, in presence of a base, such as lithium diisopropylamide.

Scheme 3

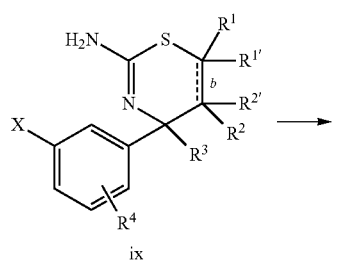

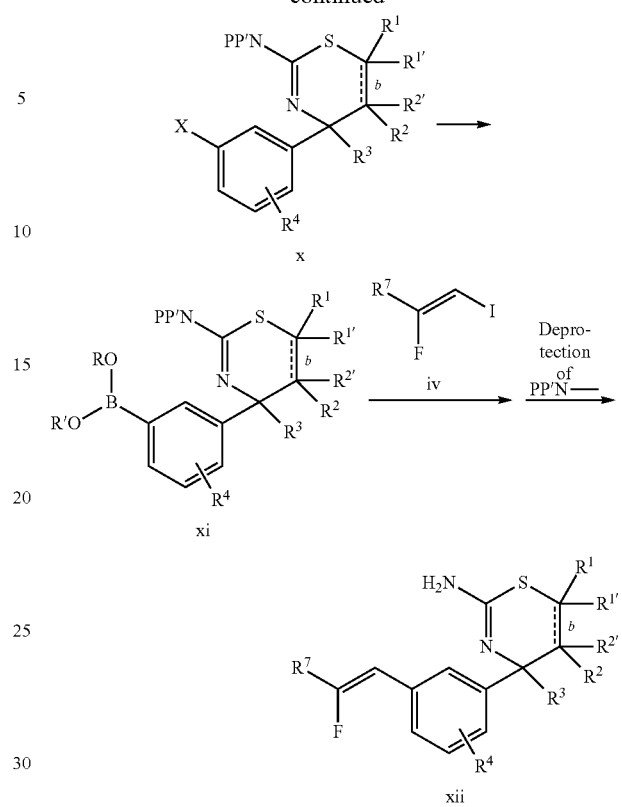

The final compound xii may be synthesized as shown in Scheme 3. First, the free amino group of compound ix, wherein X is Cl, Br, or I, is suitably protected, for example by reaction with di-tert-butyl dicarbonate in presence of a base, such as N,N-diisopropylethylamine (Hünig's base). The suitably protected compound x is then transformed into boronic acid xi, for example by reacting bis(pinacolato) diboron in presence of a base, such as potassium acetate, and a suitable palladium catalyst, such [1,1'-bis(diphenylphosphino)ferrocene]-dichloropalladium(II). The final compound xii is obtained by reacting boronic acid xi with compound iv under Suzuki conditions, in presence of, for example, bis(di-tert-butyl(4-dimethylaminophenyl)phosphine)-dichloropalladium(II) and a base, such as potassium phosphate, followed by a deprotection of the amino group by reacting the Suzuki product with, for example, trifluoroacetic acid, if a di-BOC protecting strategy was employed.

Scheme 4

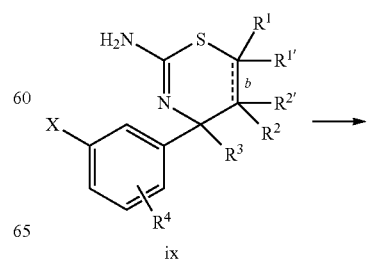

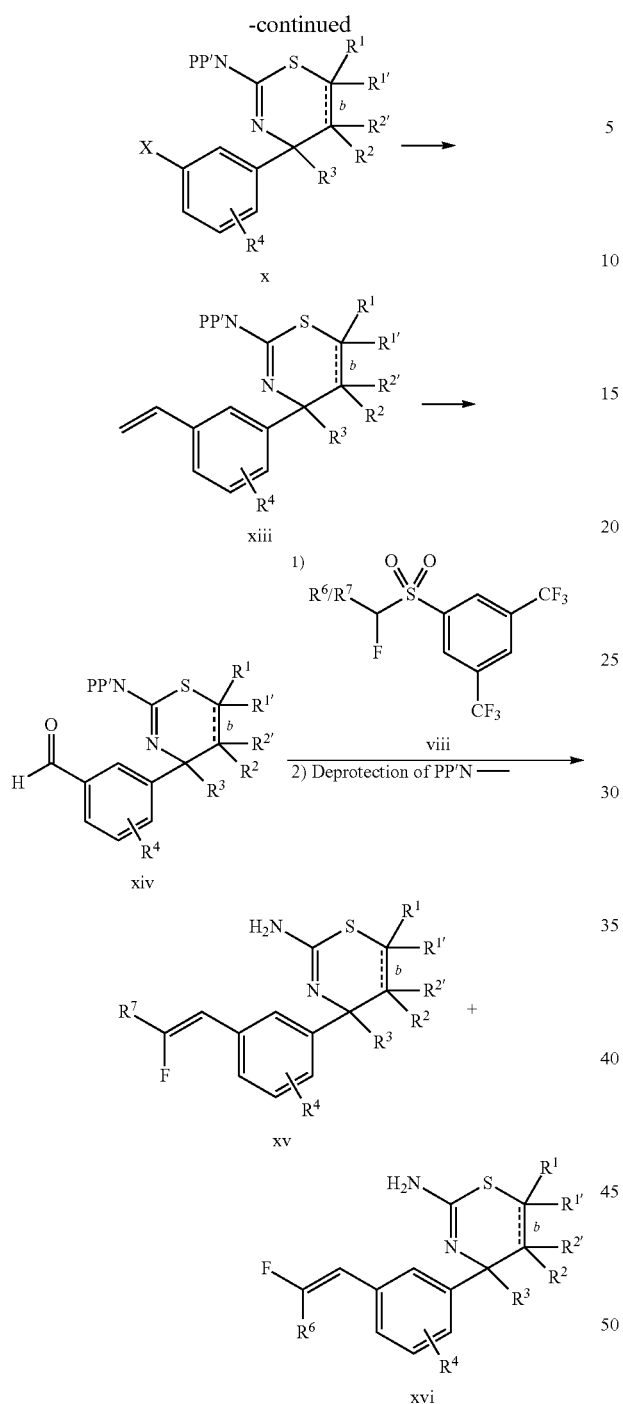

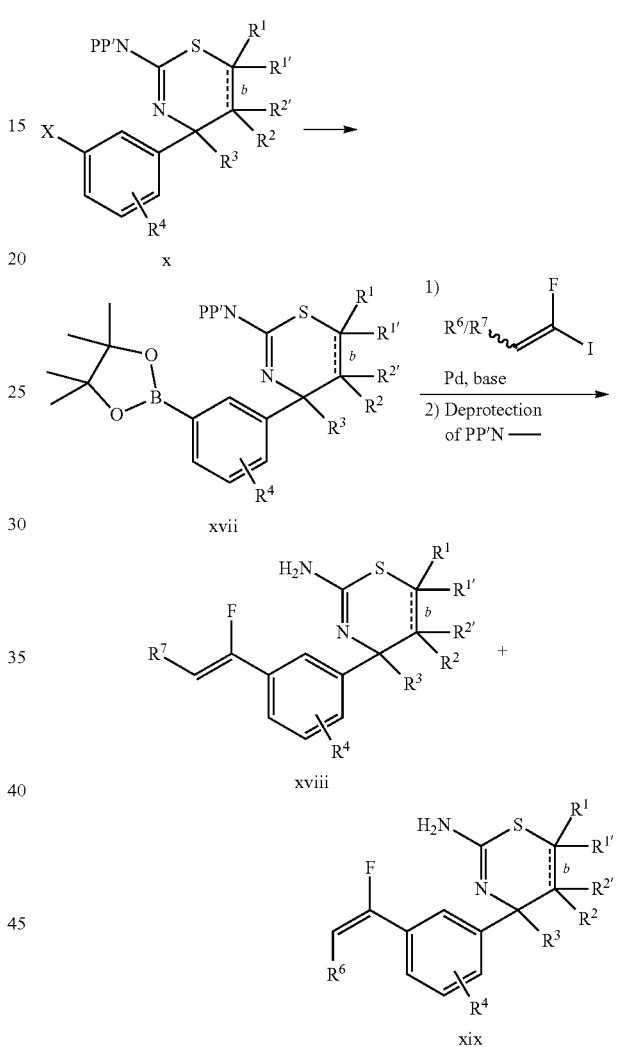

and potassium periodate. Aldehyde xiv is then reacted with compound viii in presence of a base, such as lithium bis(trimethylsilyl)amide, followed by conditions removing the protecting group(s) from the amino group using, for example, 1,8-diazabicyclo[5.4.0]undec-7-ene (DBU), if a benzoyl protecting strategy was employed, giving final compound(s) xv and/or xvi.

Scheme 5

The final compounds xviii and xix may be synthesized as shown in Scheme 5. The suitably protected compound x is transformed into boronic ester xvii by reacting compound x with, for example, bispinacolatodioron in presence of a base, such as potassium acetate, and a suitable palladium catalyst, such as bis(di-tert-butyl(4-dimethylaminophenyl)phosphine)-dichloropalladium(II). Boronic ester xvii is then coupled to a suitable vinyl iodide, for example, in presence of a base, such as potassium acetate, and a suitable palladium catalyst, such as bis(di-tert-butyl(4-dimethylaminophenyl)phosphine)-dichloropalladium(II). The vinyl iodide may be synthesized by methods known in the art. Applying conditions removing the protecting group(s) from the amino group using, for example, 1,8-diazabicyclo[5.4.0]undec-7-ene (DBU), if a benzoyl protecting strategy was employed, gives final compound(s) xviii and/or xix.

The final compounds xv and xvi may be synthesized as shown in Scheme 4. First, the free amino group of compound ix is suitably protected, for example by reaction with benzoic anhydride in presence of a base, such as trimethylamine. The suitably protected compound x is then transformed into alkene xiii by reacting compound x with, for example, potassium vinyltrifluoroborate in presence of a base, such as potassium acetate, and a suitable palladium catalyst, such as bis(di-tert-butyl(4-dimethylaminophenyl)phosphine)-dichloropalladium(II). Aldehyde xiv is obtained by subjecting alkene xiii to oxidizing conditions using, for example osmiumtetroxide, 4-methylmorpholine-N-oxide, As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds disclosed herein, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

All synthetic procedures described herein can be carried out under known reaction conditions, advantageously under those described herein, either in the absence or in the presence (usually) of solvents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependent on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize the compounds provided herein include, but are not limited to, water; esters, including lower alkyl-lower alkanoates, for example, EtOAc; ethers including aliphatic ethers, for example, $Et_2O$ and ethylene glycol dimethylether or cyclic ethers, for example, THF; liquid aromatic hydrocarbons, for example, benzene, toluene and xylene; alcohols, for example, MeOH, EtOH, 1-propanol, iPrOH, n- and t-butanol; nitriles, for example, $CH_3CN$; halogenated hydrocarbons, for example, $CH_2Cl_2$, $CHCl_3$ and $CCl_4$; acid amides, for example, DMF; sulfoxides, for example, DMSO; bases, including heterocyclic nitrogen bases, for example, pyridine; carboxylic acids, for example, lower alkanecarboxylic acids, for example, AcOH; inorganic acids, for example, HCl, HBr, HF, and $H_2SO_4$; carboxylic acid anhydrides, for example, lower alkane acid anhydrides, for example, acetic anhydride; cyclic, linear, or branched hydrocarbons, for example, cyclohexane, hexane, pentane, and isopentane; and mixtures of any of these solvents, such as purely organic solvent combinations, or water-containing solvent combinations, for example, aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (for example, liquid and gas phase), extraction, distillation, trituration, and reverse phase HPLC. Reactions conditions such as temperature, duration, pressure, and atmosphere (inert gas, ambient) are known in the art and may be adjusted as appropriate for the reaction.

The disclosure further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the scope of this disclosure.

Further, processes for making and further reacting these intermediates are also understood to be encompassed in the scope of this disclosure.

Also provided herein are new starting materials and/or intermediates, as well as processes for the preparation thereof. In select embodiments, such starting materials are used and reaction conditions so selected as to obtain the desired compound(s). Starting materials are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

EXAMPLES

This section provides specific examples of compounds of Formula I and methods of making the same.

List of Abbreviations

TABLE 1

| ACN | acetonitrile |
|---|---|
| COMU | (1-Cyano-2-ethoxy-2-oxoethylidenaminooxy)dimethylaminomorpholino-carbenium hexafluorophosphate |
| DCM | dichloromethane |
| DMA | dimethylacetamide |
| DMF | dimethylformamide |
| DMSO | dimethylsulfoxide |
| EtOAc | ethyl acetate |
| EtOH | ethanol |
| KOAc | potassium acetate |

TABLE 1-continued

| LDA | lithium iisopropylamide |
|---|---|
| Pd(AmPhos)Cl$_2$ | bis(di-tert-butyl(4-dimethylaminophenyl)phosphine)dichloropalladium(II) |
| Pd$_2$(dba)$_3$ | tris(dibenzylideneacetone)dipalladium(0) |
| Pyr | pyridine |
| TFA | tifluoroacetic acid |
| Tf$_2$O | tifluoromethanesulfonic anhydride |
| THF | tetrahydrofuran |
| T$_3$P | propylphosphonic anhydride |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, 0-40% EtOAc/hexane) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 mL/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were collected on a Bruker NMR instrument at 300 MHz or 400 MHz. Where so characterized, all observed protons are reported as parts-per-million (ppm) downfield from tetramethylsilane (TMS) or other internal reference in the appropriate solvent indicated.

$^{19}$F NMR Spectra:

Unless otherwise indicated, all $^{19}$F NMR spectra were collected on a Bruker NMR instrument at 376 MHz. All observed protons are reported as parts-per-million (ppm) downfield.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

Compound Names

The compounds disclosed and described herein have been named using either (1) the naming convention provided with Chem-Draw Ultra 12.0.3. software, available in Chem Office, or (2) by the ISIS database software (Advanced Chemistry Design Labs or ACD software).

Specific Examples

Provided in this section are the procedures to synthesize specific examples of the compounds provided herein. All starting materials are either commercially available from Sigma-Aldrich Chemical Company, Inc., St. Louis, Mo., USA, unless otherwise noted, or known in the art and may be synthesized by employing known procedures using ordinary skill.

Intermediates

Intermediate 1: (Z)-5-chloro-2-(1-fluoro-2-iodovinyl)pyridine

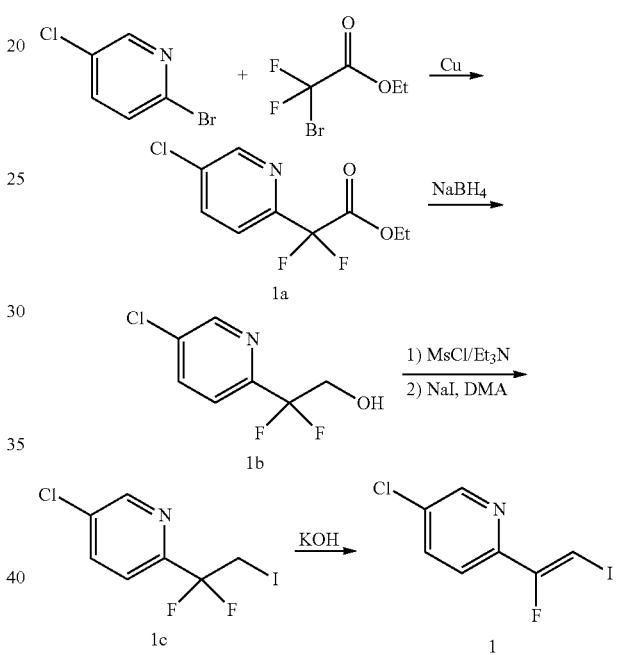

Preparation of ethyl 2-(5-chloropyridin-2-yl)-2,2-difluoroacetate (1a)

Ethyl 2-bromo-2,2-difluoroacetate (105 g, 520 mmol) was added slowly to a suspension of copper(0) powder (66.0 g, 1039 mmol) in DMSO (1.2 L) under nitrogen atmosphere at room temperature. The reaction mixture was stirred at room temperature for 1 hour and 2-bromo-5-chloropyridine (Shanghai Fchemicals Technology Co., Ltd., Shanghai, China) (50.0 g, 260 mmol) was added in one portion. The reaction mixture was stirred at room temperature for 12 hours. It was filtered through a pad of Celite and the filtrate was partitioned between ethyl acetate (1 L) and sat'd ammonium chloride (100 mL) and water (100 mL). The organic layer was separated and the aqueous layer was extracted with ethyl acetate (2×100 mL). The combined organic solution was washed with water (2×100 mL), dried over Na$_2$SO$_4$ and concentrated. Purification of the residue by silica gel chromatography (0 to 10% ethyl acetate in hexanes) gave 1a (60 g, 64% yield) as a clear liquid. MS (ESI +ve ion) m/z: [M+1]=236.0. $^1$H NMR (400 MHz, Chloroform-d) δ 8.63-8.59 (m, 1H), 7.85 (dt, J=8.4, 1.6 Hz, 1H), 7.70 (dt, J=8.4, 0.9 Hz, 1H), 4.11 (q, J=7.1, 1.0 Hz, 2H), 1.26 (t, J=7.1, 1.0 Hz, 3H).

Preparation of 2-(5-chloropyridin-2-yl)-2,2-difluoro-ethane-1-ol (1b)

To a solution of 1a (47.0 g, 199 mmol) in ethanol (600 mL) at 0° C. was added sodium borohydride (7.5 g, 199 mmol) portion-wise. The reaction mixture was stirred at room temperature for 1 hour. It was quenched with water (500 mL) and concentrated under reduced pressure. The crude material was diluted with water (500 mL) and extracted with ethyl acetate (2×500 mL). The combined organic extracts were dried over $Na_2SO_4$ and concentrated. Purification of the residue by silica gel chromatography (0 to 10% ethyl acetate in hexanes) gave 1b (35 g, 91% yield) as a light yellow solid. MS (ESI +ve ion) m/z: [M+1]=194.2. $^1$H NMR (400 MHz, Chloroform-d) δ 8.64-8.58 (m, 1H), 7.86 (dd, J=8.4, 2.4 Hz, 1H), 7.70 (dt, J=8.5, 1.5 Hz, 1H), 4.24 (t, J=12.4 Hz, 2H). Note: OH proton was not observed.

Preparation of 5-chloro-2-(1,1-difluoro-2-iodoethyl)pyridine (1c)

To a solution of 1b (31 g, 160 mmol) in DCM (500 mL) at 0° C. was added triethylamine (49.1 mL, 352 mmol) followed by dropwise addition of methanesulfonyl chloride (23.7 mL, 304 mmol). The reaction mixture was stirred at room temperature for 1 hour. The reaction mixture was diluted with water (500 mL) and extracted with DCM (2×500 mL). The combined organic extracts were washed with brine (250 mL), dried over $Na_2SO_4$ and concentrated under reduced pressure. The residue was dissolved in N,N-dimethyl acetamide (600 mL) and treated with sodium iodide (96 g, 641 mol) portion-wise. The reaction mixture was heated at 110° C. for 36 hours. It was cooled to room temperature, diluted with water (500 mL), and extracted with ethyl acetate (2×500 mL). The combined organic layers were washed with brine (500 mL), dried over $Na_2SO_4$ and concentrated under reduced pressure. The residue was purified by silica gel chromatography (0 to 10% ethyl acetate in hexanes) to give 1c (30 g, 60% yield) as a brown solid. MS (ESI +ve ion) m/z: [M+1]=303.9. $^1$H NMR (400 MHz, Chloroform-d) δ 8.59 (s, 1H), 7.87-7.84 (m, 1H), 7.27 (d, J=2.0 Hz, 1H), 4.27 (t, J=12.4 Hz, 2H).

Preparation of (Z)-5-chloro-2-(1-fluoro-2-iodovinyl)pyridine (1)

To a solution of 1c (30 g, 99 mmol) in DMSO (50 mL) at 0° C. was added a solution of KOH (19.4 g, 346 mmol) in water (50 mL) dropwise. The reaction mixture was stirred at room temperature for 10 hours. It was diluted with water (150 mL) and stirred for 15 minutes. The precipitated solids were collected by filtration, washed with water (2×100 mL), and dried to afford (Z)-5-chloro-2-(1-fluoro-2-iodovinyl)pyridine (1, 24.7 g, 87% yield) as a white crystalline solid. MS (ESI +ve ion) m/z: [M+1]=284.0. $^1$H NMR (400 MHz, Chloroform-d) δ 8.54-8.51 (m, 1H), 7.74 (dd, J=8.5, 2.4 Hz, 1H), 7.50 (ddd, J=8.5, 1.8, 0.8 Hz, 1H), 6.94 (d, J=34.3 Hz, 1H).

Intermediate 2: (Z)-6-(1-fluoro-2-iodovinyl)nicotinonitrile

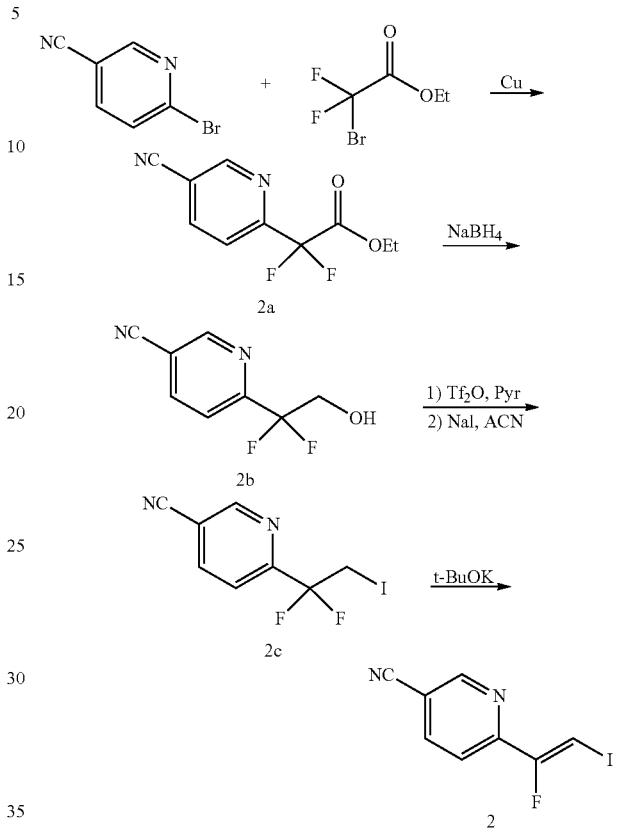

Preparation of ethyl 2-(5-cyanopyridin-2-yl)-2,2-difluoroacetate (2a)

To a suspension of copper(0) powder (Spectrochem PVT. LTD., Mumbai, India) (413 g, 6557 mmol) in dimethyl sulfoxide (6 L) was added ethyl 2-bromo-2,2-difluoroacetate (Matrix Scientific, Columbia, S.C., USA) (665 g, 3279 mmol) dropwise under nitrogen atmosphere at room temperature. The reaction mixture was stirred at room temperature for 1 hour and 2-bromo-5-cyanopyridine (Sigma-Aldrich, St. Louis, Mo., USA) (300 g, 1639 mmol) was added portion-wise. The reaction mixture was stirred at room temperature for 12 hours. It was filtered through a pad of celite and the filtrate was partitioned between ethyl acetate (3 L) and sat'd ammonium chloride (2.5 mL) solution. The organic layer was separated and the aqueous layer was extracted with ethyl acetate (2×2 L). The combined organic layers were washed with water (2×2 L), dried over $Na_2SO_4$ and concentrated under reduced pressure. The residue was purified by silica gel column chromatography (0 to 10% ethyl acetate in hexanes) to give 2a (320 g, 86% yield) as a colourless oil. MS (ESI +ve ion) m/z: [M+1]=227.1. $^1$H NMR (400 MHz, Chloroform-d) δ 8.93 (d, J=2.0 Hz, 1H), 8.18 (dd, J=8.2, 2.1 Hz, 1H), 7.90 (dd, J=8.1, 1.0 Hz, 1H), 4.39 (q, J=7.1 Hz, 2H), 1.34 (t, J=7.1 Hz, 3H).

Preparation of 6-(1,1-difluoro-2-hydroxyethyl)nicotinonitrile (2b)

To a solution of 2a (105 g, 464 mmol) in THF (1.5 L) was added sodium borohydride (10.5 g, 279 mmol) portion-wise at −20° C. The reaction mixture was stirred at −20° C. for 30 minutes and methanol (525 mL) was added dropwise at −20° C. The reaction mixture was stirred at −20° C. for 1 hour, and quenched with water (500 mL). It was concentrated under reduced pressure. The residue was diluted with water (0.5 L) and extracted with ethyl acetate (2×1 L). The combined organic solution was dried over $Na_2SO_4$ and concentrated. The residue was purified by silica gel column chromatography (0 to 25% ethyl acetate in hexanes) to provide 2b (43.0 g, 50% yield) as a light-yellow solid. MS (ESI +ve ion) m/z: [M+1]=185.1. $^1$H NMR (400 MHz, Chloroform-d) δ 8.97-8.90 (m, 1H), 8.18 (dd, J=8.2, 2.1 Hz, 1H), 7.89 (dd, J=8.3, 0.9 Hz, 1H), 4.29 (t, J=12.4 Hz, 2H). Note: OH proton was not observed.

Preparation of 6-(1,1-difluoro-2-iodoethyl)nicotinonitrile (2c)

To a solution of 2b (87 g, 472 mmol) in acetonitrile (1.3 L) was added pyridine (74.7 g, 945 mmol) followed by dropwise addition of triflouoromethanesulfonic anhydride (Sigma-Aldrich, St. Louis, Mo., USA) (240 g, 850 mmol) at −10° C. under nitrogen atmosphere. The reaction mixture was stirred at room temperature for 5 hours. It was cooled to 0° C. and sodium iodide (354 g, 2362 mmol) was added portion-wise. The reaction mixture was heated at 60° C. for 2 hours. It was cooled to room temperature, diluted with water (2 L) and extracted with ethyl acetate (3×3 L). The combined organic solution was dried over $Na_2SO_4$ and concentrated under reduced pressure. The crude material was purified on a silica gel column (0 to 10% ethyl acetate in hexanes) to afford 2c (107 g, 77% yield) as a light-yellow solid. MS (ESI +ve ion) m/z: [M+1]=295.0. $^1$H NMR (400 MHz, Chloroform-d) δ 8.95 (s, 1H), 8.17-8.14 (m, 1H), 7.87-7.85 (d, J=8.0 Hz, 1H), 3.97 (t, J=14.4 Hz, 2H).

Preparation of 6-(1,1-difluoro-2-iodoethyl)nicotinonitrile (2)

To a solution of 2c (58 g, 197 mmol) in THF (580 mL) was added potassium tert-butoxide (26.6 g, 237 mmol) portion-wise at 0° C. The reaction mixture was stirred at 0° C. for 2 hours, and quenched with sat'd aqueous $NH_4Cl$ (100 mL) and water (100 mL). It was extracted with ethyl acetate (3×700 mL). The combined organic extracts were dried over $Na_2SO_4$ and concentrated. Purification of the residue by silica gel chromatography (0 to 5% ethyl acetate in hexanes) gave 6-(1,1-difluoro-2-iodoethyl)nicotinonitrile (2, 33 g, 61% yield) as a light yellow solid. MS (ESI +ve ion) m/z: [M+1]=274.9. $^1$H NMR (400 MHz, DMSO-$d_6$) δ 9.04 (dd, J=2.1, 1.0 Hz, 1H), 8.45 (dd, J=8.3, 2.1 Hz, 1H), 7.81 (dt, J=8.3, 1.1 Hz, 1H), 7.42 (d, J=36.4 Hz, 1H).

Intermediate (3): (Z)-2-chloro-5-(1-fluoro-2-iodovinyl)pyrazine

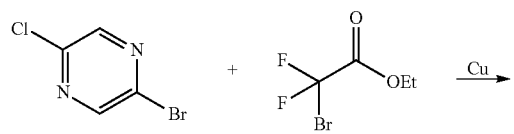

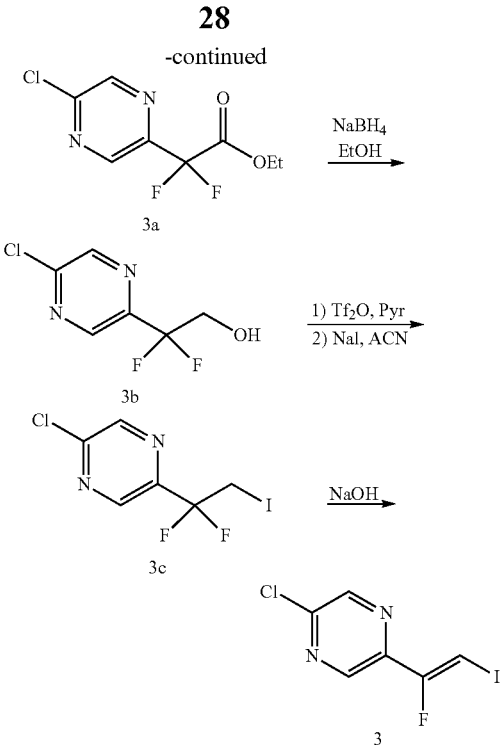

Preparation of ethyl 2-(5-chloropyrazin-2-yl)-2,2-difluoroacetate (3a)

To a suspension of copper(0) powder (244 g, 3877 mmol) in DMSO (5 L) was added ethyl 2-bromo-2,2-difluoroacetate (394 g, 1939 mmol) at room temperature. The reaction mixture was stirred at room temperature for 1 hour and 2-bromo-5-chloropyrazine (Shanghai Fchemicals Technology Co., Ltd., Shanghai, China) (250 g, 1292 mmol) was added in a portion-wise manner. The reaction mixture was stirred at room temperature for 3 hours then quenched with sat'd aqueous ammonia chloride (2.0 L). The mixture was filtered through a celite pad and the filtrate was extracted with ethyl acetate (2×2 L). The combined organic layers were dried over $Na_2SO_4$ and concentrated under reduced pressure. The residue was purified by silica gel chromatography (0 to 2% ethyl acetate in hexanes) to afford 3a (215 g, 70% yield) as a viscous colorless liquid. $^1$H NMR (400 MHz, DMSO-$d_6$) δ 9.05 (d, J=1.4 Hz, 1H), 8.98 (dd, J=1.4, 0.7 Hz, 1H), 4.39-4.34 (m, 2H), 1.24 (t, J=7.1 Hz, 3H).

Preparation of 2-(5-chloropyrazin-2-yl)-2,2-difluoroethanol (3b)

To a solution of 3a (215 g, 909 mmol) in ethanol (400 mL) was added sodium borohydride (34.4 g, 909 mmol) in a portion-wise manner at 0° C. After the reaction mixture was stirred for 30 minutes at 0° C., it was quenched with water (200 mL) and the mixture was concentrated under reduced pressure. The residue was diluted with water (750 mL) and extracted with ethyl acetate (2×1.0 L). The combined organic solution was dried over $Na_2SO_4$ and concentrated under reduced pressure. The residue was purified by silica gel chromatography (0 to 10% ethyl acetate in hexanes) to afford 3b (130 g, 73% yield) as a colorless liquid. MS (ESI +ve ion) m/z: [M+1]=195.0. $^1$H NMR (300 MHz, DMSO-d$_6$) δ 8.97 (dt, J=1.4, 0.7 Hz, 1H), 8.82 (d, J=1.4 Hz, 1H), 5.70 (t, J=6.4 Hz, 1H), 4.01 (td, J=13.8, 6.4 Hz, 2H).

Preparation of 2-chloro-5-(1,1-difluoro-2-iodoethyl)pyrazine (3c)

To a solution of 3b (130 g, 668 mmol) in acetonitrile (1.3 L) at 0° C. was added pyridine (54.0 mL, 668 mmol) followed by dropwise addition of triflic anhydride (147 mL, 869 mmol). The reaction mixture was stirred at 0° C. for 30 minutes then room temperature for 10 minutes. It was treated with sodium iodide (300 g, 2004 mmol) portion-wise at room temperature then stirred at 70° C. for 2 hours. After cooling to room temperature, the reaction was quenched with sat'd aqueous sodium thuiosulfate solution (2.0 L) and extracted with ethyl acetate (2×2.0 L). The combined organic layers were washed with brine (2.0 L), dried over Na$_2$SO$_4$ and concentrated under reduced pressure. The residue was purified by silica gel chromatography (2% ethyl acetate in hexanes) to afford 3c (150.0 g, 71% yield) as a yellow solid. $^1$H NMR (300 MHz, DMSO-d$_6$) δ 8.96 (s, 1H), 8.89 (s, 1H), 4.07 (t, J=16.4 Hz, 2H).

Preparation of (Z)-2-chloro-5-(1-fluoro-2-iodovinyl)pyrazine (3)

To a solution of 3c (150 g, 493 mmol) in DMSO (900 mL) was added 5.0 M aqueous NaOH solution (148 mL, 740 mmol). The reaction mixture was stirred at 0° C. for 2 hours then quenched with water (100 mL) and extracted with EtOAc (2×200 mL). The combined organic layers were washed with brine (300 mL), dried over Na$_2$SO$_4$ and concentrated under reduced pressure. The residue was purified by silica gel chromatography (0 to 5% ethyl acetate in hexanes) to afford (Z)-2-chloro-5-(1-fluoro-2-iodovinyl)pyrazine (3, 78 g, 54% yield) as a white solid. $^1$H NMR (400 MHz, Chloroform-d) δ 8.59 (q, J=1.4 Hz, 1H), 8.54 (q, J=1.4 Hz, 1H), 7.05 (dd, J=34.1, 1.3 Hz, 1H).

EXAMPLES

Example 100: (S,Z)-4-(5-(2-(5-chloropyridin-2-yl)-2-fluorovinyl)-2-fluorophenyl)-4-methyl-4H-1,3-thiazin-2-amine

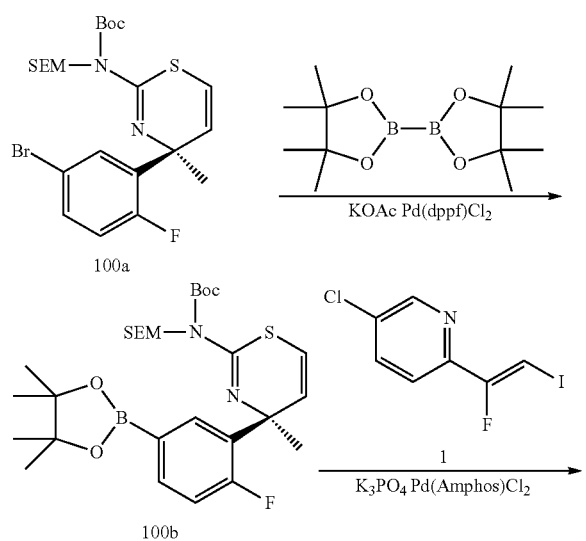

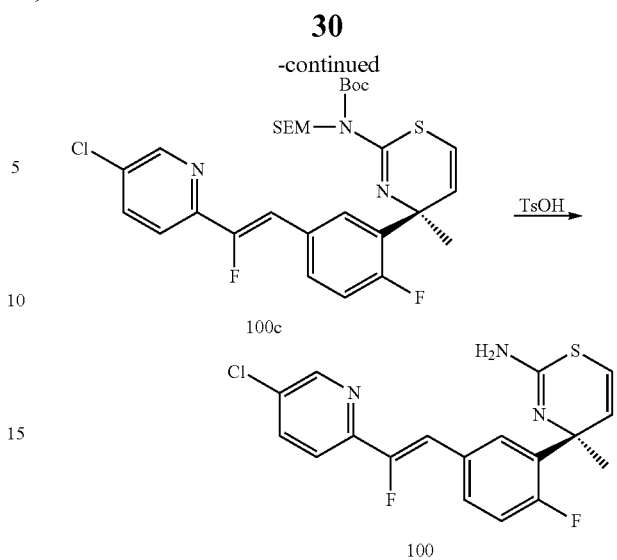

Preparation of (S)-tert-butyl (4-(2-fluoro-5-(4,4,5,5-tetramethyl-1,3,2-dioxaborolan-2-yl)phenyl)-4-methyl-4H-1,3-thiazin-2-yl)((2-(trimethylsilyl)ethoxy)methyl)carbamate (100b)

A mixture of (S)-tert-butyl (4-(5-bromo-2-fluorophenyl)-4-methyl-4H-1,3-thiazin-2-yl)((2-(trimethylsilyl)ethoxy)methyl)carbamate (100a, prepared according to the methods described in WO 2016022724) (1.07 g, 2.01 mmol), dioxane (11 mL), bis(pinacolato)diboron (0.66 g, 2.62 mmol), potassium acetate (592 mg, 6.04 mmol) was purged with argon for 5 minutes then treated with [1,1'-bis(diphenylphosphino)ferrocene]-dichloropalladium (II) complex with dichloromethane (0.12 g, 0.14 mmol). The mixture was heated to 85° C. for 1.5 hours. After cooling to room temperature, the mixture was filtered through a pad of celite and the cake was washed with EtOAc. The filtrate was concentrated in vacuo to afford (S)-tert-butyl (4-(2-fluoro-5-(4,4,5,5-tetramethyl-1,3,2-dioxaborolan-2-yl)phenyl)-4-methyl-4H-1,3-thiazin-2-yl)((2-(trimethylsilyl)ethoxy)methyl)carbamate (100b) as a dark brown oil, which was used as crude assuming theoretical yield. MS (ESI +ve ion) m/z: [M+1]=579.

Preparation of (S,Z)-tert-butyl (4-(5-(2-(5-chloropyridin-2-yl)-2-fluorovinyl)-2-fluorophenyl)-4-methyl-4H-1,3-thiazin-2-yl)((2-(trimethylsilyl)ethoxy)methyl) carbamate (100c)

A mixture of (S)-tert-butyl (4-(2-fluoro-5-(4,4,5,5-tetramethyl-1,3,2-dioxaborolan-2-yl)phenyl)-4-methyl-4H-1,3-thiazin-2-yl)((2-(trimethylsilyl)ethoxy)methyl)carbamate (100b, 0.100 g, 0.173 mmol), (Z)-5-chloro-2-(1-fluoro-2-iodovinyl)pyridine (1, 000000000003220020.073 g, 0.259 mmol), Pd(Amphos)Cl$_2$ (Sigma-Aldrich) (0.012 g, 0.017 mmol), K$_3$PO$_4$ (110 mg, 0.519 mmol) in dioxane (1.5 mL) and water (0.25 mL) was purged with argon for 5 minutes then heated at 80° C. for 30 minutes. The mixture was diluted with water and extracted with EtOAc. The organic solution was dried over Na$_2$SO$_4$ and concentrated in vacuo. The residue was purified by silica gel chromatography (0 to 100% EtOAc in heptane) to afford (S,Z)-tert-butyl (4-(5-(2-(5-chloropyridin-2-yl)-2-fluorovinyl)-2-fluorophenyl)-4-methyl-4H-1,3-thiazin-2-yl)((2-(trimethylsilyl)ethoxy)methyl) carbamate (100c, 58.4 mg, 56% yield) as a white solid. MS (ESI +ve ion) m/z: [M+1]=608.

Preparation of Example 100

A mixture of (S,Z)-tert-butyl (4-(5-(2-(5-chloropyridin-2-yl)-2-fluorovinyl)-2-fluorophenyl)-4-methyl-4H-1,3-thiazin-2-yl)((2-(trimethylsilyl)ethoxy)methyl)carbamate (100c, 58.4 mg, 0.096 mmol), p-toluenesulfonic acid monohydrate (0.055 g, 0.288 mmol) and dioxane (1.5 mL) was heated to 80° C. for 2.5 hours. The mixture was diluted with sat'd aqueous $Na_2CO_3$ solution and extracted with EtOAc. The organic solution was dried over $Na_2SO_4$ and concentrated in vacuo. The residue was purified by silica gel chromatography twice (first time using 0 to 100% EtOAc/EtOH (3:1) in heptane as the gradient, second time using 0 to 100% EtOAc in DCM as the gradient) to provide (S,Z)-4-(5-(2-(5-chloropyridin-2-yl)-2-fluorovinyl)-2-fluorophenyl)-4-methyl-4H-1,3-thiazin-2-amine (Example 100, 22 mg, 60% yield) as an off-white solid. MS (ESI +ve ion) m/z: [M+1]=378. $^1$H NMR (400 MHz, Chloroform-d) δ 8.54 (s, 1H), 7.72 (ddd, J=2.15, 5.33, 7.97 Hz, 2H), 7.57-7.64 (m, 1H), 7.54 (dd, J=0.98, 8.41 Hz, 1H), 6.92-7.10 (m, 2H), 6.23-6.35 (m, 2H), 4.46 (br s, 2H), 1.74 (s, 3H). $^{19}$F NMR (376 MHz, Chloroform-d) 6-110.77 (d, J=1.73 Hz, 1F),-124.20 (d, J=1.73 Hz, 1F).

Example 101: (S,Z)-6-(2-(3-(2-amino-4-methyl-4H-1,3-thiazin-4-yl)-4-fluorophenyl)-1-fluorovinyl)nicotinonitrile

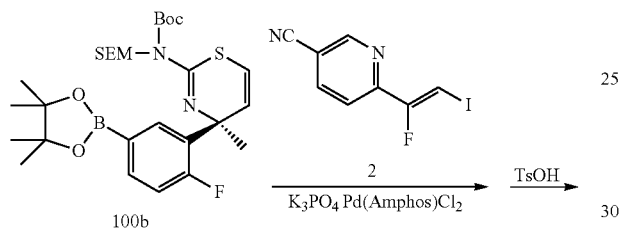

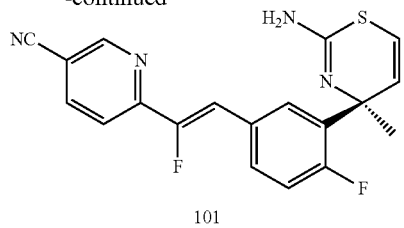

This compound (32 mg, 69% overall yield) as a white solid was prepared in a fashion similar to that described for Example 100, here starting from boronic ester 100b (106 mg, 0.18 mmol) and vinyl iodide 2 (65 mg, 0.24 mmol). MS (ESI +ve ion) m/z: [M+1]=369. $^1$H NMR (400 MHz, Chloroform-d) δ 8.82 (d, J=0.98 Hz, 1H), 8.01 (dd, J=2.05, 8.31 Hz, 1H), 7.77 (dd, J=2.15, 7.82 Hz, 1H), 7.60-7.71 (m, 2H), 7.23 (d, J=36.39 Hz, 1H), 7.07 (dd, J=8.61, 11.35 Hz, 1H), 6.25-6.34 (m, 2H), 1.74 (s, 3H). $NH_2$ was not clear in NMR. $^{19}$F NMR (376 MHz, Chloroform-d) 6-109.27 (d, J=2.60 Hz, 1F),-125.67 (d, J=2.60 Hz, 1F).

Example 102: (S,Z)-4-(5-(2-(5-chloropyridin-2-yl)-2-fluorovinyl)-2-fluorophenyl)-4-methyl-5,6-dihydro-4H-1,3-thiazin-2-amine

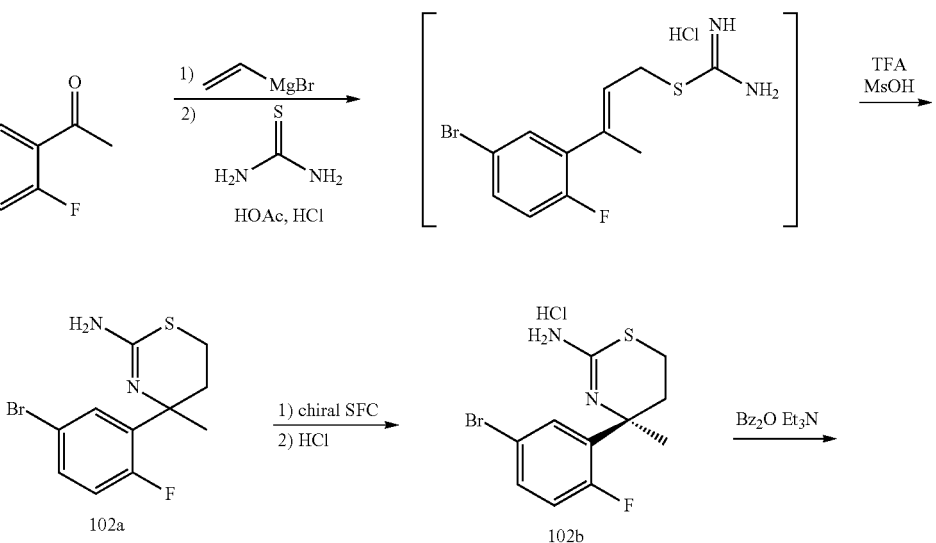

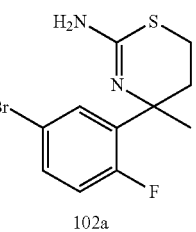

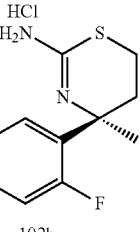

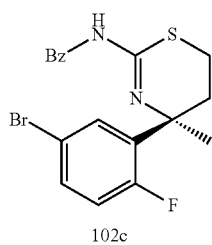

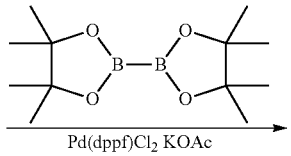

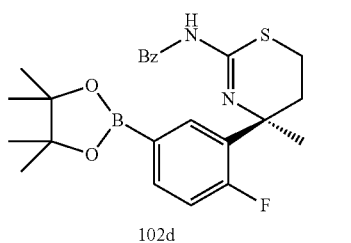

102d

-continued

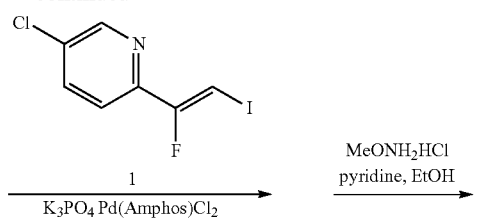

1

$\xrightarrow{K_3PO_4 \ Pd(Amphos)Cl_2}$ $\xrightarrow{\text{MeONH}_2\text{HCl} \\ \text{pyridine, EtOH}}$

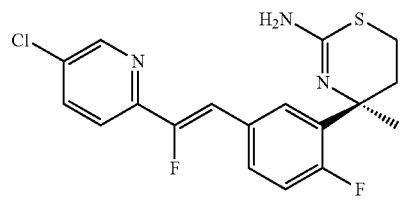

102

Preparation of (S)-4-(5-bromo-2-fluorophenyl)-4-methyl-5,6-dihydro-4H-1,3-thiazin-2-amine HCl salt (102b)

To a 500 mL 3 necked round-bottomed flask equipped with a mechanical stirrer, a nitrogen gas inlet and a temperature probe, was charged 1-(5-bromo-2-fluorophenyl)-1-ethanone (9.8 g, 45.2 mmol, AAT Pharmaceuticals) and Me-THF (100 mL). The mixture was cooled to −20° C. and was added vinylmagnesium chloride, 1.6 m solution in tetrahydrofuran (39.5 mL, 63.2 mmol, Sigma Aldrich) slowly so the temperature was controlled below −10° C. The reaction was then warmed up to 0° C. and stirred for 2 hours. The reaction was cooled to 0° C. and quenched with 40 mL 5 wt % NH$_4$Cl solution. The mixture was stirred at room temperature and the two phases were separated. The organic layer was washed with brine (300 mL) and concentrated to afford 2-(5-bromo-2-fluorophenyl)but-3-en-2-ol (12.0 g, ~100% yield) as an oil.

To a mixture of 2-(5-bromo-2-fluorophenyl)but-3-en-2-ol (58.04 g, 237 mmol) and thiourea (36.02 g, 473 mmol) at room temperature was added acetic acid (475 mL, 237 mmol) followed by 5 M aqueous HCl (48 mL, 240 mmol). The reaction mixture was heated at 50° C. for 3 days and concentrated. The residue was diluted with toluene (200 mL) and concentrated in vacuo to give (E)-3-(5-bromo-2-fluorophenyl)but-2-en-1-yl carbamimidothioate hydrochloride (80.0 g, 236 mmol) as an off-white solid which was used as crude.

To a solution of (E)-3-(5-bromo-2-fluorophenyl)but-2-en-1-yl carbamimidothioate hydrochloride (80.0 g, 236 mmol) in trifluoroacetic acid (470 mL, 236 mmol) was added methanesulfonic acid (61 mL, 940 mmol). The reaction mixture was heated at 60° C. for 2.5 days then concentrated in vacuo. The residue was taken up in EtOAc then basified via dropwise addition of 5 M aqueous NaOH until pH >10. The aqueous phase was extracted with EtOAc (2×) and the combined organic extracts were washed with brine, dried over MgSO$_4$, filtered, and concentrated. Purification of the residue by silica gel chromatography (10 to 50% EtOAc (10% MeOH [2 M NH$_3$]) in hexane) gave 4-(5-bromo-2-fluorophenyl)-4-methyl-5,6-dihydro-4H-1,3-thiazin-2-amine (102a, 47.6 g, 67% yield) as a pale brown solid. The material was subjected to chiral SFC to provide (S)-4-(5-bromo-2-fluorophenyl)-4-methyl-5,6-dihydro-4H-1,3-thiazin-2-amine (first eluting peak) as a pale orange oil which was converted to (S)-4-(5-bromo-2-fluorophenyl)-4-methyl-5,6-dihydro-4H-1,3-thiazin-2-amine hydrochloride salt (102b, 24.98 g) as an off-white solid. MS (ESI +ve ion) m/z: [M+1]=303/305. SFC conditions: CHIRALPAK AS-H column (5 μM, 21×250 mm, S/N=5172); wave length=224 nmM; mobile phase=(30% MeOH with 0.2% diethylamine, 70% carbon dioxide); flowrate=60 mL/min; pressure=172 Bar; T=40° C.

Preparation of (S)—N-(4-(5-bromo-2-fluorophenyl)-4-methyl-5,6-dihydro-4H-1,3-thiazin-2-yl)benzamide (102c)

To a mixture of (S)-4-(5-bromo-2-fluorophenyl)-4-methyl-5,6-dihydro-4H-1,3-thiazin-2-amine hydrochloride (102b, 1.50 g, 4.42 mmol) in DMF (15 mL) under N$_2$ was added triethylamine (1.54 mL, 11.04 mmol) and benzoic anhydride (1.34 g, 5.92 mmol). The mixture was stirred at room temperature overnight, then diluted with sat'd aqueous Na$_2$CO$_3$ and extracted with EtOAc. The organic solution was washed with water followed by brine, dried over Na$_2$SO$_4$ and concentrated in vacuo. The residue was purified by silica gel chromatography (0 to 60% EtOAc in heptane) to give (S)—N-(4-(5-bromo-2-fluorophenyl)-4-methyl-5,6-dihydro-4H-1,3-thiazin-2-yl)benzamide (102c, 1.66 g, 92% yield) as a white solid. MS (ESI +ve ion) m/z: [M+1]=407, 409. $^1$H NMR (400 MHz, Chloroform-d) δ 12.04-12.59 (m, 1H), 8.23 (d, J=7.24 Hz, 2H), 7.36-7.55 (m, 5H), 6.92-7.06 (m, 1H), 2.84-2.99 (m, 2H), 2.63-2.79 (m, 1H), 2.06-2.19 (m, 1H), 1.80 (s, 3H). $^{19}$F NMR (376 MHz, Chloroform-d) δ -113.63 (s).

Preparation of Example 102

A mixture of (S)—N-(4-(5-bromo-2-fluorophenyl)-4-methyl-5,6-dihydro-4H-1,3-thiazin-2-yl)benzamide (102c, 0.84 g, 2.06 mmol), bis(pinacolato)diboron (0.68 g, 2.68 mmol), and potassium acetate (0.61 g, 6.19 mmol) in 1,4-dioxane (15 mL) was purged with argon, then [1,1'-bis(diphenylphosphino)ferrocene]-dichloropalladium(II) complex with dichloromethane (0.084 g, 0.103 mmol) was added. The mixture was heated at 100° C. for 2.5 hours, cooled to room temperature, filtered through celite and the cake was washed with EtOAc. The filtrate was concentrated in vacuo to give (S)—N-(4-(2-fluoro-5-(4,4,5,5-tetramethyl-1,3,2-dioxaborolan-2-yl)phenyl)-4-methyl-5,6-dihydro-4H-

1,3-thiazin-2-yl)benzamide (102d) which was used as crude. MS (ESI +ve ion) m/z: [M+1]=455.

A mixture of 102d (0.300 g, 0.66 mmol), vinyl iodide (1, 0.187 g, 0.66 mmol), Pd(Amphos)Cl$_2$ (0.023 g, 0.033 mmol), potassium phosphate tribasic (420 mg, 1.98 mmol) in dioxane (1.5 mL) and water (0.25 mL) was purged with argon then heated to 80° C. for 30 minutes. The mixture was diluted with water and extracted with EtOAc. The organic solution was dried over Na$_2$SO$_4$ and concentrated in vacuo. The residue was purified by silica gel chromatography (0 to 100% EtOAc in heptane) to give (S,Z)—N-(4-(5-(2-(5-chloropyridin-2-yl)-2-fluorovinyl)-2-fluorophenyl)-4-methyl-5,6-dihydro-4H-1,3-thiazin-2-yl)benzamide (171 mg, 54% yield) as a yellow solid. MS (ESI +ve ion) m/z: [M+1]=484.

A mixture of (S,Z)—N-(4-(5-(2-(5-chloropyridin-2-yl)-2-fluorovinyl)-2-fluorophenyl)-4-methyl-5,6-dihydro-4H-1,3-thiazin-2-yl)benzamide (170 mg, 0.35 mmol), O-methylhydroxylamine hydrochloride (0.29 g, 3.51 mmol), and pyridine (0.278 g, 3.51 mmol) in EtOH (3 mL) was heated to 70° C. for 1 hour. The mixture was concentrated in vacuo. The residue was diluted with sat'd aqueous Na$_2$CO$_3$ and extracted with EtOAc. The organic solution was dried over Na$_2$SO$_4$ and concentrated in vacuo. The residue was purified by silica gel chromatography (0 to 100% EtOAc/EtOH (3:1) in heptane) to afford (S,Z)-4-(5-(2-(5-chloropyridin-2-yl)-2-fluorovinyl)-2-fluorophenyl)-4-methyl-5,6-dihydro-4H-1,3-thiazin-2-amine (Example 102, 78 mg, 58% yield) as an off-white solid. MS (ESI +ve ion) m/z: [M+1]=380. $^1$H NMR (400 MHz, Chloroform-d) δ 8.54 (s, 1H), 7.72 (dd, J=2.45, 8.51 Hz, 1H), 7.59-7.70 (m, 2H), 7.53-7.58 (m, 1H), 6.96-7.11 (m, 2H), 2.95 (ddd, J=3.72, 6.26, 12.13 Hz, 1H), 2.70 (dt, J=3.52, 11.64 Hz, 1H), 2.47 (ddd, J=3.52, 6.06, 13.89 Hz, 1H), 1.89 (ddd, J=3.52, 10.76, 14.08 Hz, 1H), 1.64 (s, 3H). NH$_2$ was not clear in NMR. $^{19}$F NMR (376 MHz, Chloroform-d) δ -111.21 (s, 1F), -124.00 (br. s., 1F).

Example 103: (S,Z)-6-(2-(3-(2-amino-4-methyl-5,6-dihydro-4H-1,3-thiazin-4-yl)-4-fluorophenyl)-1-fluorovinyl)nicotinonitrile

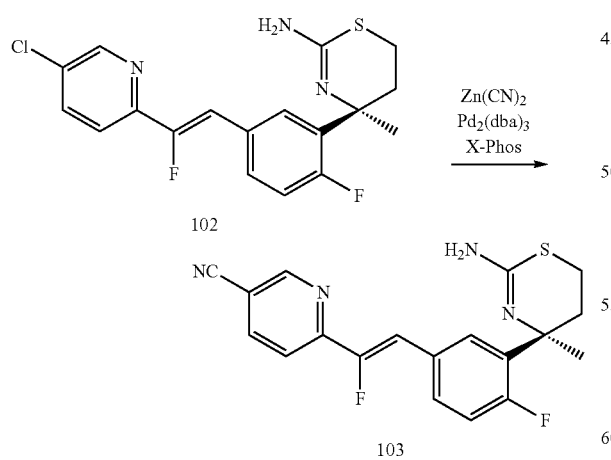

A 20 mL vial was charged with Example 102 (58 mg, 0.15 mmol), zinc cyanide (54 mg, 0.45 mmol), 2-(dicyclohexylphosphino)-2',6'-dimethoxy-1,1'-biphenyl (19 mg, 0.046 mmol), Pd$_2$(dba)$_3$ (21 mg, 0.023 mmol) and DMA (3 mL). The vial was purged with argon and sealed. The mixture was heated at 120° C. for 3.5 hours, cooled to room temperature, filtered through a bed of celite and the cake was washed with EtOAc. The filtrate was washed with water and brine, dried over Na$_2$SO$_4$, and concentrated in vacuo. The residue was purified by silica gel chromatography (0 to 100% EtOAc/EtOH (3:1) in heptane) to give the title compound (Example 103, 40.8 mg, 72% yield) as a yellow solid. MS (ESI +ve ion) m/z: [M+1]=371. $^1$H NMR (400 MHz, Chloroform-d) δ 8.83 (s, 1H), 8.01 (dd, J=2.05, 8.31 Hz, 1H), 7.69 (t, J=7.04 Hz, 3H), 7.25 (d, J=39.32 Hz, 1H), 7.04-7.12 (m, J=8.71, 11.83 Hz, 1H), 2.97 (dt, J=3.72, 6.06 Hz, 1H), 2.70 (dt, J=3.52, 11.44 Hz, 1H), 2.45 (ddd, J=3.62, 6.31, 13.94 Hz, 1H), 1.92 (ddd, J=3.62, 10.71, 14.04 Hz, 1H), 1.64 (s, 3H). NH$_2$ was not clear in NMR. $^{19}$F NMR (376 MHz, Chloroform-d) δ -109.73 (d, J=1.73 Hz, 1F), -125.55 (br. s., 1F).

Example 104: (4S,6R)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate; and Example 105: (4S,6S)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate

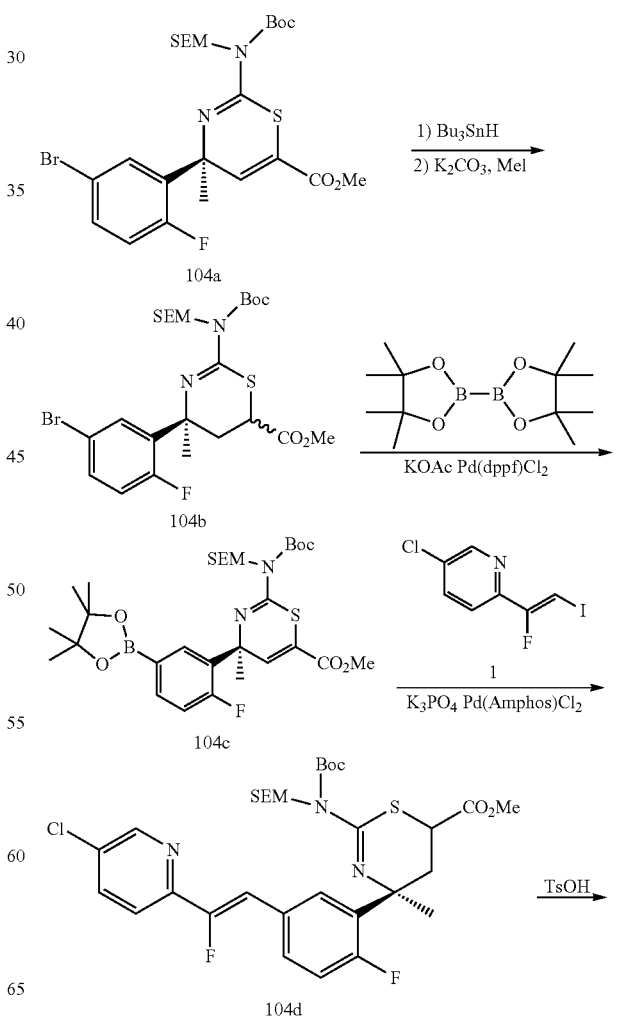

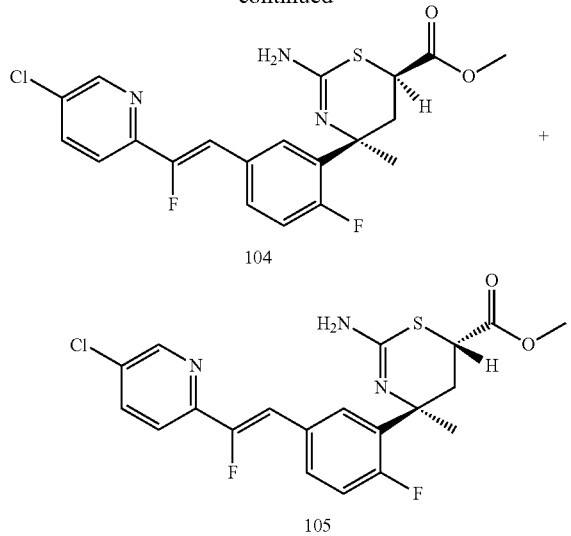

Preparation of (4S)-methyl 4-(5-bromo-2-fluorophenyl)-2-((tert-butoxycarbonyl)((2-(trimethylsilyl)ethoxy)methyl)amino)-4-methyl-5,6-dihydro-4H-1,3-thiazine-6-carboxylate (104b)

A mixture of (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (104a, prepared according to the methods described in WO 2016022724) (3.58 g, 6.07 mmol) and tributyltin hydride (Sigma-Aldrich) (5.72 mL, 21.25 mmol) in methanol (12 mL) was stirred at room temperature for 3 days then concentrated in vacuo. The residue was dissolved in DMF (10 mL) and potassium carbonate (0.42 g, 3.04 mmol) was added, followed by iodomethane (0.38 mL, 6.07 mmol). The mixture was stirred at room temperature for 1 hour then diluted with water and extracted with EtOAc (3×). The organic solution was dried over $Na_2SO_4$ and concentrated in vacuo. The residue was purified by silica gel chromatography (0 to 25% EtOAc in heptane) to give 2 eluents: the $1^{st}$ eluent was the recovered 104a (1.48 g) as a colorless oil, MS (ESI +ve ion) m/z: [M+1]=589/591; the $2^{nd}$ eluent was (4S)-methyl 4-(5-bromo-2-fluorophenyl)-2-((tert-butoxycarbonyl)((2-(trimethylsilyl)ethoxy)methyl)amino)-4-methyl-5,6-dihydro-4H-1,3-thiazine-6-carboxylate (104b, 1.17 g, 33% yield, as a mixture of two diastereomers) as a colorless oil, MS (ESI +ve ion) m/z: [M+1]=591/593.

Preparation of (4S)-methyl 2-((tert-butoxycarbonyl)((2-(trimethylsilyl)ethoxy)methyl)amino)-4-(2-fluoro-5-(4,4,5,5-tetramethyl-1,3,2-dioxaborolan-2-yl)phenyl)-4-methyl-5,6-dihydro-4H-1,3-thiazine-6-carboxylate (104c)

A mixture of (4S)-methyl 4-(5-bromo-2-fluorophenyl)-2-((tert-butoxycarbonyl)((2-(trimethylsilyl)ethoxy)methyl)amino)-4-methyl-5,6-dihydro-4H-1,3-thiazine-6-carboxylate (104b, 1.17 g, 1.98 mmol), bis(pinacolato)diboron (0.66 g, 2.61 mmol), potassium acetate (0.58 g, 5.93 mmol) in 1,4-dioxane (20 mL) was purged with argon, then [1,1'-bis(diphenylphosphino)ferrocene]-dichloropalladium(II) complex with dichloromethane (0.097 g, 0.119 mmol) was added. The mixture was heated to 90° C. for 1 hour, cooled to room temperature, filtered through a pad of celite; and the cake was washed with EtOAc. The filtrate was concentrated in vacuo to give (4S)-methyl 2-((tert-butoxycarbonyl)((2-(trimethylsilyl)ethoxy)methyl)amino)-4-(2-fluoro-5-(4,4,5,5-tetramethyl-1,3,2-dioxaborolan-2-yl)phenyl)-4-methyl-5,6-dihydro-4H-1,3-thiazine-6-carboxylate (104c) which was used as crude. MS (ESI +ve ion) m/z: [M+1]=639.

Preparation of (4S)-methyl 2-((tert-butoxycarbonyl)((2-(trimethylsilyl)ethoxy)methyl)amino)-4-(5-((Z)-2-(5-chloropyridin-2-yl)-2-fluorovinyl)-2-fluorophenyl)-4-methyl-5,6-dihydro-4H-1,3-thiazine-6-carboxylate (104d)

A mixture of crude boronic ester 104c (1.26 g, 1.98 mmol), vinyl iodide (1, 1.12 g, 3.96 mmol), bis(di-tert-butyl (4-dimethylaminophenyl)phosphine)dichloropalladium(II) (0.14 g, 0.20 mmol), and potassium phosphate tribasic (1.32 g, 6.00 mmol) in 1,4-dioxane (12 mL) and water (2 mL) was purged with argon then heated to 80° C. for 30 minutes. The mixture was diluted with water and extracted with EtOAc. The organic solution was dried over $Na_2SO_4$ and concentrated in vacuo. The crude was purified by silica gel chromatography (0 to 70% EtOAc in heptane) to afford (4S)-methyl 2-((tert-butoxycarbonyl)((2-(trimethylsilyl)ethoxy)methyl)amino)-4-(5-((Z)-2-(5-chloropyridin-2-yl)-2-fluorovinyl)-2-fluorophenyl)-4-methyl-5,6-dihydro-4H-1,3-thiazine-6-carboxylate (104d, 1.11 g, 84% yield over two steps) as a beige solid. MS (ESI +ve ion) m/z: [M+1]=668.

Preparation of Examples 104 and 105

A mixture of (4S)-methyl 2-((tert-butoxycarbonyl)((2-(trimethylsilyl)ethoxy)methyl)amino)-4-(5-((Z)-2-(5-chloropyridin-2-yl)-2-fluorovinyl)-2-fluorophenyl)-4-methyl-5,6-dihydro-4H-1,3-thiazine-6-carboxylate (104d, 0.572 g, 0.856 mmol) and 4-methylbenzenesulfonic acid hydrate (0.407 g, 2.141 mmol) in 1,4-dioxane (5 mL) was heated to 90° C. for 1 hour. The mixture was concentrated in vacuo and the residue was treated with a few drops of conc. sulfuric acid (bubbles were formed). The mixture was neutralized with sat'd aqueous $Na_2CO_3$ and extracted with EtOAc. The organic solution was dried over $Na_2SO_4$ and concentrated in vacuo. The residue was purified by silica gel chromatography (0 to 100% EtOAc in DCM) to give a diastereomeric mixture of 104 and 105 (153 mg, 41% yield).

A small amount of the diastereomeric mixture was subjected to reverse phase HPLC to provide Examples 104 and 105. The relative stereochemistry was arbitrarily assigned. (4S,6R)-Methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate (104): MS (ESI +ve ion) m/z: [M+1]=438. $^1$H NMR (400 MHz, CHLOROFORM-d) δ 8.54 (d, J=2.35 Hz, 1H), 7.91 (dd, J 1.96, 8.02 Hz, 1H), 7.72 (dd, J=2.45, 8.51 Hz, 1H), 7.65 (ddd, J=2.25, 4.60, 8.41 Hz, 1H), 7.55 (dd, J=1.27, 8.51 Hz, 1H), 6.98-7.13 (m, 2H), 4.24-4.31 (m, 1H), 3.67 (s, 3H), 2.67 (dd, J=4.11, 13.89 Hz, 1H), 1.87-2.01 (m, 1H), 1.60 (s, 3H). $NH_2$ was not clear. $^{19}$F NMR (376 MHz, Chloroform-d) δ −111.32 (s, 1F), −124.18 (br. s., 1F). (4S,6S)-Methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate (105): MS (ESI +ve ion) m/z: [M+1]=438. $^1$H NMR (400 MHz, Chloroform-d) δ 8.51-8.57 (m, 1H), 7.73 (dd, J=2.45, 8.51 Hz, 1H), 7.67 (ddd, J=2.35, 4.65, 8.46 Hz, 1H), 7.56 (dd, J=1.37, 8.41 Hz, 1H), 7.46 (dd, J=2.15, 8.02 Hz, 1H), 6.93-7.12 (m, 2H), 3.73 (s, 3H), 3.60 (dd, J=3.52, 12.72 Hz, 1H), 3.07 (dd, J=3.62, 13.99 Hz, 1H), 1.73-1.83 (m, 1H), 1.71 (d, J=0.78 Hz, 3H). NH₂ was not clear. ¹⁹F NMR (376 MHz, CHLOROFORM-d) δ-110.96 (s, 1F),−123.74 (br. s., 1F).

Example 106: (4S,6S)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate; and Example 107: (4S,6R)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate

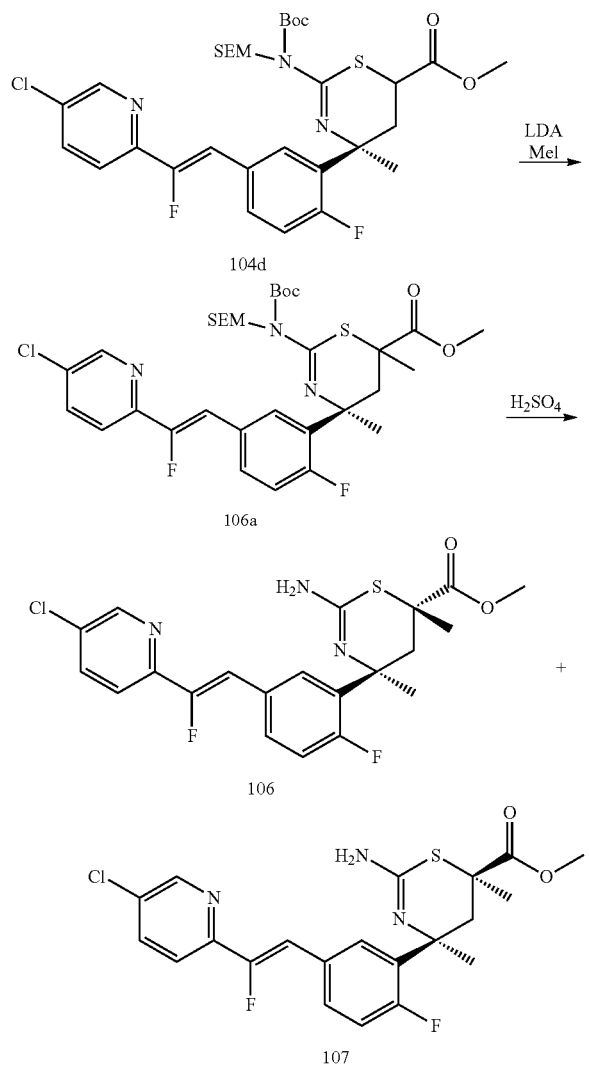

To a solution of (4S)-methyl 2-((tert-butoxycarbonyl)((2-(trimethylsilyl)ethoxy)methyl)amino)-4-(5-((Z)-2-(5-chloropyridin-2-yl)-2-fluorovinyl)-2-fluorophenyl)-4-methyl-5,6-dihydro-4H-1,3-thiazine-6-carboxylate (104d, 0.55 g, 0.82 mmol) in THF (10 mL) at −78° C. was added lithium diisopropylamide (1.64 mL of 2 M solution in THF/heptane/ethylbenzene, 3.29 mmol) dropwise. The mixture was stirred for 1 hour, then methyl iodide (0.31 mL, 4.94 mmol) was added and the mixture was gradually warmed to room temperature. The reaction was quenched with sat'd aqueous NH₄Cl solution and extracted with EtOAc. The organic layer was dried over Na₂SO₄ and concentrated in vacuo. The crude was purified by silica gel chromatography (0 to 50% EtOAc in heptane) to give (4S)-methyl 2-((tert-butoxycarbonyl)((2-(trimethylsilyl)ethoxy)methyl)amino)-4-(5-((Z)-2-(5-chloropyridin-2-yl)-2-fluorovinyl)-2-fluorophenyl)-4,6-dimethyl-5,6-dihydro-4H-1,3-thiazine-6-carboxylate (106a, 0.23 g, 41% yield) as a white solid. MS (ESI +ve ion) m/z: [M+1]=682.

A mixture of 106a (0.23 g, 0.33 mmol) and sulfuric acid (0.09 mL, 1.67 mmol) was stirred at room temperature for 30 minutes, then cooled to 0° C. and neutralized with sat'd aqueous Na₂CO₃. The mixture was extracted with EtOAc. The organic solution was dried over Na₂SO₄ and concentrated in vacuo. The residue was purified by reverse phase HPLC to provide Example 106 (48 mg, 32% yield) and 107 (33 mg, 22% yield). The relative stereochemistry was confirmed via extensive NMR studies. (4S,6S)-Methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate (106): MS (ESI +ve ion) m/z: [M+1]=452. ¹H NMR (400 MHz, CHLOROFORM-d) δ 8.54 (d, J=2.35 Hz, 1H), 7.72 (dd, J=2.45, 8.51 Hz, 1H), 7.62 (ddd, J=2.35, 4.55, 8.36 Hz, 1H), 7.55 (dd, J=1.27, 8.51 Hz, 1H), 7.45 (dd, J=2.15, 8.02 Hz, 1H), 6.93-7.07 (m, 2H), 4.63 (br. s., 2H), 3.32 (d, J=14.48 Hz, 1H), 3.01 (s, 3H), 1.72 (d, J=14.48 Hz, 1H), 1.67 (d, J=0.78 Hz, 3H), 1.58 (s, 3H). ¹⁹F NMR (376 MHz, Chloroform-d) δ −109.53 (d, J=2.60 Hz, 1F), −124.20 (br. s., 1F). (4S,6R)-Methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate (107): MS (ESI +ve ion) m/z: [M+1]=452. ¹H NMR (400 MHz, Chloroform-d) δ 8.54 (d, J=2.35 Hz, 1H), 7.69-7.77 (m, 2H), 7.63-7.68 (m, 1H), 7.56 (dd, J=1.27, 8.51 Hz, 1H), 6.96-7.10 (m, 2H), 3.78 (s, 3H), 2.63 (d, J=14.48 Hz, 1H), 1.70 (br. s., 1H), 1.59 (s, 3H), 1.36 (s, 3H). NH₂ was not clear. ¹⁹F NMR (376 MHz, Chloroform-d) δ −111.03 (br. s., 1F), −123.91 (br. s., 1F).

Example 108: (4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate; and Example 109: (4S,6S)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate

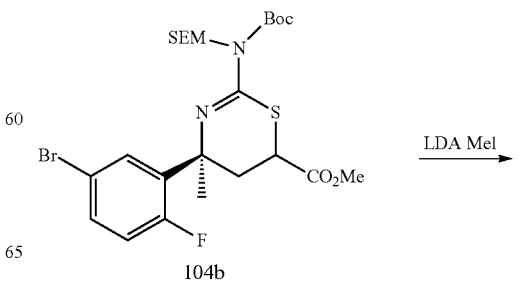

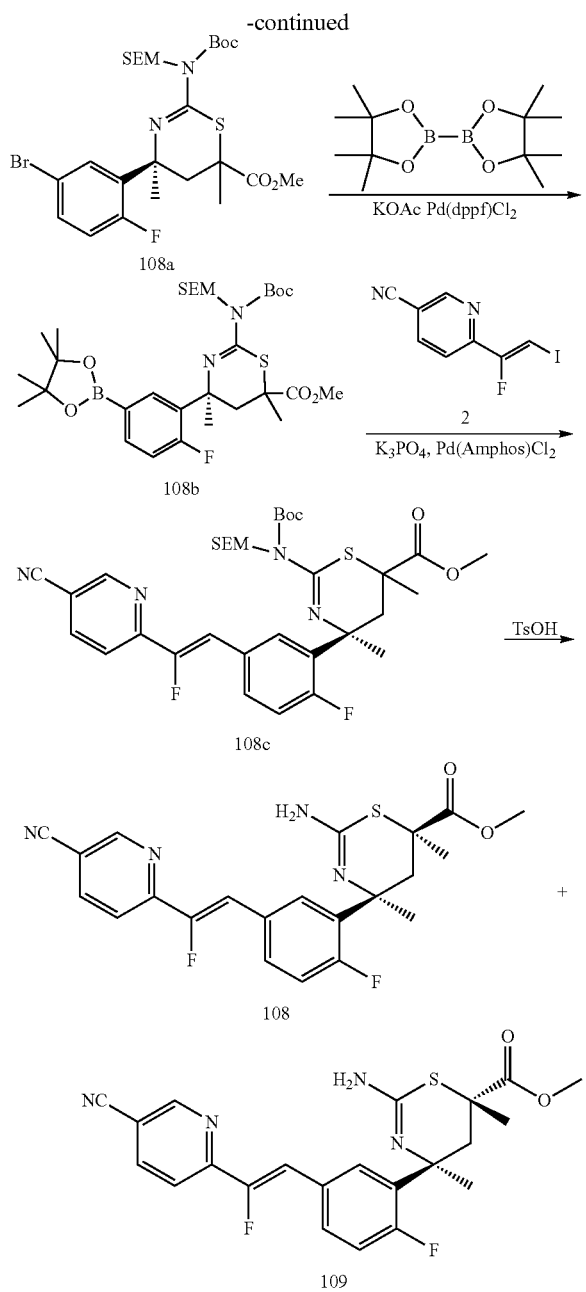

Preparation of (4S)-methyl 4-(5-bromo-2-fluorophenyl)-2-((tert-butoxycarbonyl)((2-(trimethylsilyl)ethoxy)methyl)amino)-4,6-dimethyl-5,6-dihydro-4H-1,3-thiazine-6-carboxylate (108a)

To a mixture of (4S)-methyl 4-(5-bromo-2-fluorophenyl)-2-((tert-butoxycarbonyl)((2-(trimethylsilyl)ethoxy)methyl)amino)-4-methyl-5,6-dihydro-4H-1,3-thiazine-6-carboxylate (104b, 1.54 g, 2.60 mmol) in THF (20 mL) at −78° C. was added lithium diisopropylamide (2.0 M solution in THF/heptane/ethylbenzene, 1.95 mL, 3.90 mmol). The yellow mixture was stirred for 30 minutes, then methyl iodide (0.81 mL, 13.02 mmol) was added and the mixture was gradually warmed to 0° C. After stirring at 0° C. for 1 hour, the reaction was quenched with sat'd aqueous NH$_4$Cl solution and extracted with EtOAc. The organic solution was dried over Na$_2$SO$_4$ and concentrated in vacuo. The crude was purified by silica gel chromatography (0 25% EtOAc in heptane) to provide (4S)-methyl 4-(5-bromo-2-fluorophenyl)-2-((tert-butoxycarbonyl)((2-(trimethylsilyl)ethoxy)methyl)amino)-4,6-dimethyl-5,6-dihydro-4H-1,3-thiazine-6-carboxylate (108a, 1.48 g, 94% yield) as a yellow oil. MS (ESI +ve ion) m/z: [M+1]=605/607.

Preparation of (4S)-methyl 2-((tert-butoxycarbonyl)((2-(trimethylsilyl)ethoxy)methyl)amino)-4-(2-fluoro-5-(4,4,5,5-tetramethyl-1,3,2-dioxaborolan-2-yl)phenyl)-4,6-dimethyl-5,6-dihydro-4H-1,3-thiazine-6-carboxylate (108b)

A mixture of (4S)-methyl 4-(5-bromo-2-fluorophenyl)-2-((tert-butoxycarbonyl)((2-(trimethylsilyl)ethoxy)methyl)amino)-4,6-dimethyl-5,6-dihydro-4H-1,3-thiazine-6-carboxylate (108a, 1.48 g, 2.44 mmol), bis(pinacolato)diboron (0.81 g, 3.17 mmol), potassium acetate (0.72 g, 7.32 mmol) in dioxane (25 mL) was purged with argon, then [1,1'-bis(diphenylphosphino)ferrocene]-dichloropalladium(II) complex with dichloromethane (0.12 g, 0.15 mmol) was added. The mixture was heated to 90° C. for 2.5 hours, cooled to room temperature, and filtered through celite. The cake was washed with EtOAc. The filtrate was concentrated in vacuo to provide (4S)-methyl 2-((tert-butoxycarbonyl)((2-(trimethylsilyl)ethoxy)methyl)amino)-4-(2-fluoro-5-(4,4,5,5-tetramethyl-1,3,2-dioxaborolan-2-yl)phenyl)-4,6-dimethyl-5,6-dihydro-4H-1,3-thiazine-6-carboxylate (108b) which was used as crude. MS (ESI +ve ion) m/z: [M+1]=653.

Preparation of Examples 108 and 109

A mixture of boronic ester 108b (0.500 g, 0.766 mmol), vinyl iodide 2 (0.315 g, 1.149 mmol), bis(di-tert-butyl(4-dimethylaminophenyl)phosphine)dichloropalladium(II) (0.054 g, 0.077 mmol), potassium phosphate tribasic (505 mg, 2.298 mmol) in 1,4-dioxane (6 mL) and water (1 mL) was purged with argon then heated to 80° C. for 30 minutes. The mixture was diluted with water and extracted with EtOAc. The organic solution was dried over Na$_2$SO$_4$ and concentrated in vacuo. The crude was purified by silica gel chromatography (0 to 50% EtOAc in heptane) to give (4S)-methyl 2-((tert-butoxycarbonyl)((2-(trimethylsilyl)ethoxy)methyl)amino)-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate (108c, 0.397 g, 77% yield) as a beige solid. MS (ESI +ve ion) m/z: [M+1]=673.

A mixture of (4S)-methyl 2-((tert-butoxycarbonyl)((2-(trimethylsilyl)ethoxy)methyl)amino)-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate (108c, 52.5 mg, 0.078 mmol) and p-toluenesulfonic acid monohydrate (39 mg, 0.207 mmol) in 1,4-dioxane (0.5 mL) was heated to 80° C. for 2 hours, then cooled to room temperature and quenched with sat'd aqueous Na$_2$CO$_3$. The mixture was extracted with EtOAc. The organic layer was washed with water followed by brine, dried over Na$_2$SO$_4$, filtered, and concentrated in vacuo. The residue was purified by flash chromatography on silica gel (0 to 100% EtOAc:EtOH (3:1) in heptane) to provide 2 compounds: Example 108 (12 mg, 35% yield) as a white solid and Example 109 (20 mg, 58% yield) as a white solid. The relative stereochemistry was assigned by NMR data comparison to those of Examples 106 and 107. (4S,6R)-Methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate (108): MS (ESI +ve ion) m/z: [M+1]=443. 1H NMR (400 MHz, Chloroform-d) δ 8.82 (s, 1H), 8.01 (dd, J=2.05, 8.31 Hz, 1H), 7.60-7.74 (m, 2H), 7.51 (dd, J=2.15, 8.02 Hz, 1H), 7.14-7.25 (m, 1H), 7.00-7.08 (m, 1H), 4.28-4.88 (m, 2H), 3.31 (d, J=14.28 Hz, 1H), 3.01 (s, 3H), 1.72 (d, J=14.48 Hz, 1H), 1.66 (d, J=0.78 Hz, 3H), 1.58 (s, 3H). $^{19}$F NMR (376 MHz, Chloroform-d) δ −108.03 (s, 1F), −125.68 (s, 1F). (4S,6S)-Methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate (109): MS (ESI +ve ion) m/z: [M+1]=443. $^1$H NMR (400 MHz, Chloroform-d) δ 8.82 (d, J=0.98 Hz, 1H), 8.01 (dd, J=2.05, 8.31 Hz, 1H), 7.82 (dd, J=2.05, 7.92 Hz, 1H), 7.63-7.73 (m, 2H), 7.15-7.28 (m, 1H), 7.07 (dd, J=8.51, 11.84 Hz, 1H), 4.56 (br. s, 2H), 3.79 (s, 3H), 2.66 (d, J=14.28 Hz, 1H), 2.28 (d, J=14.48 Hz, 1H), 1.57 (s, 3H), 1.37 (s, 3H). $^{19}$F NMR (376 MHz, Chloroform-d) δ −109.48 (d, J=1.73 Hz, 1F), −125.51 (d, J=1.73 Hz, 1F).

Example 110: 6-((Z)-2-(3-((4S,6S)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile

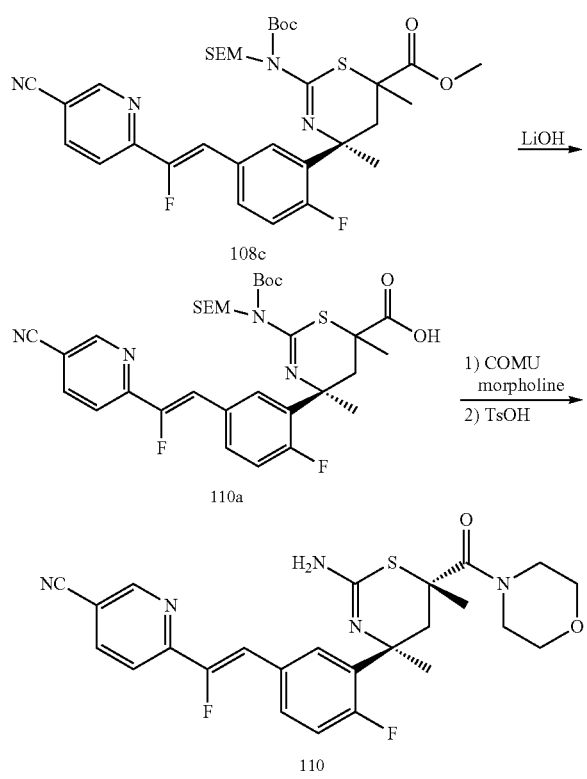

A mixture of 108c (0.300 g, 0.446 mmol) and lithium hydroxide hydrate (0.037 g, 0.892 mmol) in THF (3 mL) and water (3 mL) was stirred at room temperature for 2 hours. The mixture was neutralized with 1 N HCl (3 mL) then concentrated in vacuo to give acid 110a which was used as crude.

(1-Cyano-2-ethoxy-2-oxoethylidenaminooxy)dimethylaminomorpholinocarbenium hexafluorophosphate (COMU) (Acros Organics) (0.520 g, 1.214 mmol) was added to a solution of crude 110a and morpholine (0.317 mL, 3.64 mmol) in DMF (3 mL) at room temperature. After 2 hours, the reaction mixture was diluted with sat'd aqueous Na$_2$CO$_3$ and EtOAc. The organic layer was washed with water followed by brine, dried over Na$_2$SO$_4$, filtered, and concentrated in vacuo. The resulting yellow oil was taken up in 1,4-dioxane (3 mL) and treated with p-toluenesulfonic acid monohydrate (0.289 g, 1.518 mmol). The mixture was heated to 80° C. for 2 hours, diluted with sat'd aqueous Na$_2$CO$_3$ and EtOAc. The organic layer was washed with brine, dried over Na$_2$SO$_4$, filtered, and concentrated in vacuo. The residue was purified by silica gel chromatography: 0-100% EtOAc in heptane. The product was obtained as off-white semi-solid. The product was further purified by reverse phase preparative HPLC (Gemini column (5 micron, C18, 150×30 mm) eluting at 45 mL/min with a linear gradient of 10% (v/v) to 100% MeCN (0.1% v/v TFA) in water (0.1% TFA) over 20 minutes) to afford 6-((Z)-2-(3-((4S,6S)-2-amino-4,6-dimethyl-6-(4-morpholinylcarbonyl)-5,6-dihydro-4H-1,3-thiazin-4-yl)-4-fluorophenyl)-1-fluoroethenyl)-3-pyridinecarbonitrile (110, 11 mg, 4% yield) as a white solid. Structure confirmed by both 2D NMR and X-Ray analysis. MS (ESI +ve ion) m/z: [M+1]=498. $^1$H NMR (400 MHz, Chloroform-d) δ 8.82 (s, 1H), 8.01 (dd, J=2.05, 8.31 Hz, 1H), 7.74 (dd, J=2.05, 7.92 Hz, 1H), 7.62-7.70 (m, 2H), 7.15-7.26 (m, 1H), 7.06 (dd, J=8.51, 11.84 Hz, 1H), 3.59-3.74 (m, 8H), 2.73 (d, J=14.87 Hz, 1H), 2.42 (d, J=14.87 Hz, 1H), 1.66 (s, 3H), 1.26 (s, 3H). NH$_2$ was not clear. $^{19}$F NMR (376 MHz, Chloroform-d) δ −108.90 (s, 1F), −125.45 (s, 1F). The relative stereochemistry of Example 110 was confirmed by an X-ray crystal structure and NMR studies.

Example 111: 6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile

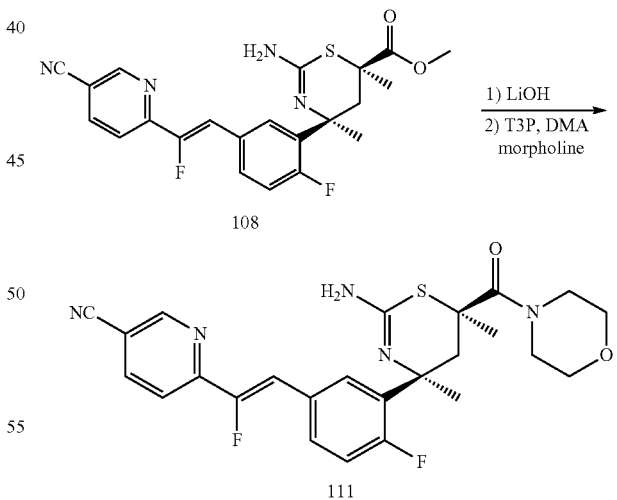

A mixture of (4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate (108, 38 mg, 0.086 mmol) and lithium hydroxide hydrate (12 mg, 0.274 mmol) in THF (0.3 mL), acetonitrile (0.3 mL) and water (0.2 mL) was stirred at room temperature for 2 hours then treated with HCl (0.3 mL of 1 M solution) and concentrated in vacuo. Ether was added and the mixture concentrated to give (4S,6R)-2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylic acid (37 mg, 100%) as a yellow solid which was used as crude. MS (ESI +ve ion) m/z: [M+1]=429.

A mixture of (4S,6R)-2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylic acid (37 mg, 0.086 mmol), propylphosphonic anhydride solution (Sigma-Aldrich) (50 wt. % in ethyl acetate, 0.22 mL, 0.345 mmol), and morpholine (0.10 mL, 1.123 mmol) in DMA (2 mL) was stirred at room temperature overnight. The mixture was filtered and the cake washed with MeOH. The filtrate was concentrated and the residue was purified by reverse phase HPLC (0-80% water in MeCN with 0.1% TFA). The fractions were neutralized with 1 N NaOH and extracted with DCM. The organic solution was concentrated to give 6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile (Example 111, 10 mg, 23% yield) as a white solid. MS (ESI +ve ion) m/z: [M+1]=498. $^1$H NMR (400 MHz, Chloroform-d) δ 8.82 (s, 1H), 8.01 (dd, J=2.15, 8.22 Hz, 1H), 7.58-7.73 (m, 3H), 7.15-7.27 (m, 1H), 7.06 (dd, J=8.22, 11.93 Hz, 1H), 4.57 (br. s., 2H), 3.44-3.58 (m, 4H), 3.31 (br. s., 4H), 3.02 (d, J=14.48 Hz, 1H), 1.99 (d, J=14.48 Hz, 1H), 1.70 (s, 6H). $^{19}$F NMR (376 MHz, Chloroform-d) δ −108.05 (br. s., 1F), −125.98 (s, 1F). The relative stereochemistry of Example 111 was established by NMR studies and in comparison to the NMR data of Example 110.

Example 112: (4S,6R)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide; and Example 113: (4S,6S)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide

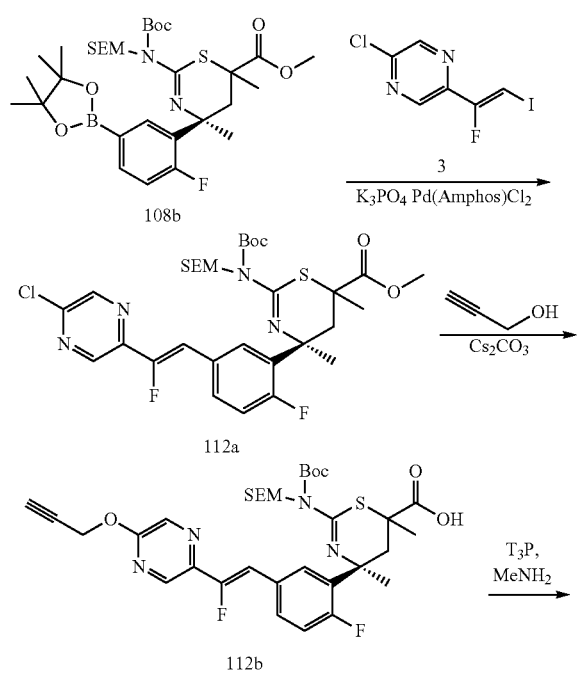

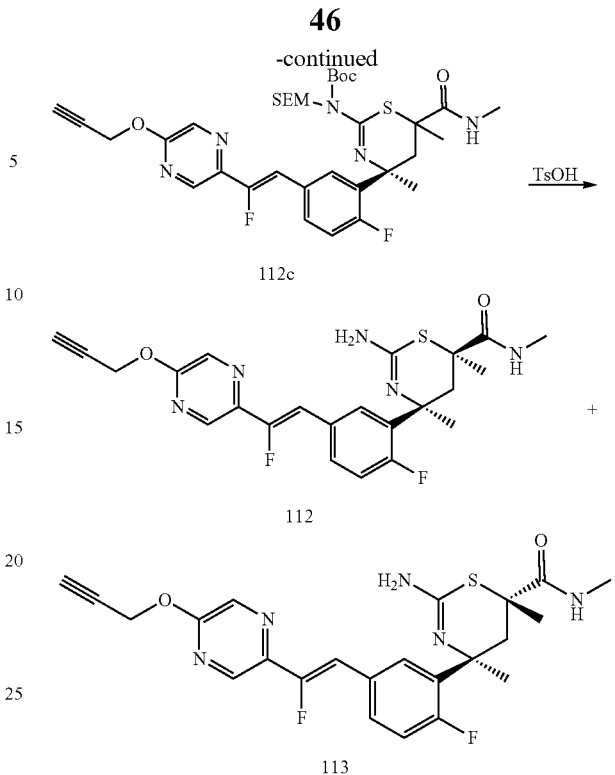

Preparation of (4S)-methyl 2-((tert-butoxycarbonyl) ((2-(trimethylsilyl)ethoxy)methyl)amino)-4-(5-((Z)-2-(5-chloropyrazin-2-yl)-2-fluorovinyl)-2-fluorophenyl)-4,6-dimethyl-5,6-dihydro-4H-1,3-thiazine-6-carboxylate (112a)

A mixture of boronic ester 108b (3.11 g, 4.76 mmol), vinyl iodide 3 (2.51 g, 8.81 mmol), bis(di-tert-butyl(4-dimethylaminophenyl)phosphine)dichloropalladium(II) (0.30 g, 0.43 mmol), and K$_3$PO$_4$ (3.14 g, 14.28 mmol) in 1,4-dioxane (24 mL) and water (4 mL) was purged with argon then heated to 80° C. for 1 hour. The mixture was diluted with water and extracted with EtOAc. The organic solution was dried over Na$_2$SO$_4$ and concentrated in vacuo. The reside was purified by silica gel chromatography (0 to 50% EtOAc in heptane) to afford (4S)-methyl 2-((tert-butoxycarbonyl)((2-(trimethylsilyl)ethoxy)methyl)amino)-4-(5-((Z)-2-(5-chloropyrazin-2-yl)-2-fluorovinyl)-2-fluorophenyl)-4,6-dimethyl-5,6-dihydro-4H-1,3-thiazine-6-carboxylate (112a, 3.12 g, 96% yield) as a yellow solid. MS (ESI +ve ion) m/z: [M+1]=683.

Preparation of (4S)-2-((tert-butoxycarbonyl)((2-(trimethylsilyl)ethoxy)methyl)amino)-4-(2-fluoro-5-((Z)-2-fluoro-2-(5-(prop-2-yn-1-yloxy)pyrazin-2-yl) vinyl)phenyl)-4,6-dimethyl-5,6-dihydro-4H-1,3-thiazine-6-carboxylic acid (112b)

A mixture of 112a (1.02 g, 1.49 mmol), propargyl alcohol (0.924 mL, 15.630 mmol), and cesium carbonate (1.455 g, 4.470 mmol) in THF (8 mL) was heated at 70° C. overnight then cooled to room temperature and neutralized with HCl (10 mL of 1 M solution). The mixture was extracted with EtOAc. The organic solution was dried over Na$_2$SO$_4$, filtered and concentrated in vacuo. The residue was purified by silica gel chromatography (0 to 100% (EtOAc/EtOH=3/1) in DCM) to give acid 112b (0.30 g, 29% yield) as a yellow solid. MS (ESI +ve ion) m/z: [M+1]=689. The ratio of two diastereomers was about 1:6 judged by LC integration.

Preparation of Examples 112 and 113

A mixture of acid 112b (50.4 mg, 0.073 mmol), propanephosphonic acid cyclic anhydride solution (50 wt. % in ethyl acetate, 0.10 mL, 0.146 mmol), and methanamine (2.0 M solution in THF, 0.18 mL, 0.366 mmol) in DCM (0.5 mL) was stirred at room temperature for 1 hour. The reaction was quenched with sat'd aqueous NaHCO$_3$ and extracted with EtOAc. The organic layer was dried over Na$_2$SO$_4$ and concentrated in vacuo. The residue was purified by silica gel chromatography (0 to 100% EtOAc in heptane) to afford amide 112c (36.8 mg, 72%) as a white solid. MS (ESI +ve ion) m/z: [M+1]=702.

A mixture of amide 112c (32.8 mg, 0.047 mmol) and p-toluenesulfonic acid monohydrate (17 mg, 0.089 mmol) in 1,4-dioxane (1 mL) was heated at 80° C. for 1 hour. After cooling to room temperature, the mixture was neutralized with sat'd aqueous Na$_2$CO$_3$ and extracted with EtOAc. The organic phase was dried over Na$_2$SO$_4$ and concentrated in vacuo. The residue was purified by silica gel chromatography (0 to 100% EtOAc/EtOH (3:1) in heptane) to provide 2 compounds: the 1$^{st}$ eluent was Example 112 (2 mg, 9% yield) as a white solid; the 2$^{nd}$ eluent was Example 113 (12 mg, 55% yield) as a white solid. The stereochemistry was assigned based on NMR studies. (4S,6R)-2-Amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide (112): MS (ESI +ve ion) m/z: [M+1]=472. $^1$H NMR (400 MHz, Chloroform-d) δ 8.38 (s, 1H), 8.26 (s, 1H), 7.55 (ddd, J=2.25, 4.45, 8.36 Hz, 1H), 7.35 (dd, J=2.15, 7.82 Hz, 1H), 7.02 (dd, J=8.41, 11.74 Hz, 1H), 6.72-6.86 (m, 1H), 6.51 (d, J=4.69 Hz, 1H), 5.00-5.06 (m, 2H), 5.00-5.06 (m, 2H), 3.52 (d, J=14.28 Hz, 1H), 2.81-2.87 (m, 1H), 2.49-2.56 (m, 1H), 2.08 (d, J=4.70 Hz, 3H), 1.66 (s, 3H), 1.55 (s, 3H). $^{19}$F NMR (376 MHz, Chloroform-d) δ -108.28 (br. s., 1F), -126.46 (d, J=40.75 Hz, 1F). (4S,6S)-2-Amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide (113): MS (ESI +ve ion) m/z: [M+1]=472. $^1$H NMR (400 MHz, Chloroform-d) δ 8.38 (s, 1H), 8.26 (s, 1H), 7.76 (dd, J=2.15, 7.82 Hz, 1H), 7.61 (ddd, J=2.25, 4.60, 8.41 Hz, 1H), 7.05 (dd, J=8.51, 11.64 Hz, 2H), 6.74-6.93 (m, 1H), 5.03 (d, J=2.35 Hz, 2H), 3.09 (d, J=14.09 Hz, 1H), 2.85 (d, J=4.89 Hz, 3H), 2.53 (t, J=2.35 Hz, 1H), 1.69 (d, J=14.09 Hz, 1H), 1.50 (s, 3H), 1.49 (br. s., 3H). NH$_2$ was not clear. $^{19}$F NMR (376 MHz, Chloroform-d) δ -110.85 (br. s., 1F), -125.90 (d, J=39.88 Hz, 1F).

Example 114: ((4S,6S)-2-amino-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazin-6-yl)(morpholino)methanone

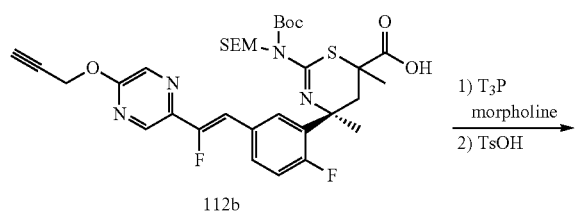

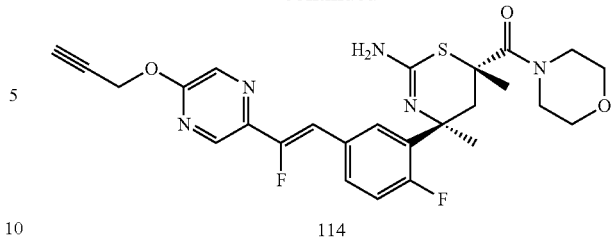

This compound (10 mg, 26% overall yield) as a white solid was prepared in a fashion similar to that described for Example 113, here starting from morpholine (13 mg, 0.146 mmol) and acid 112b (50 mg, 0.073 mmol). MS (ESI +ve ion) m/z: [M+1]=528. $^1$H NMR (400 MHz, Chloroform-d) δ 8.37 (s, 1H), 8.25 (s, 1H), 7.58-7.69 (m, 2H), 7.04 (dd, J=8.31, 11.84 Hz, 1H), 6.75-6.92 (m, 1H), 5.03 (d, J=2.35 Hz, 2H), 3.66 (dd, J=4.21, 17.31 Hz, 8H), 2.77 (d, J=14.67 Hz, 1H), 2.53 (t, J=2.35 Hz, 1H), 2.37 (d, J=14.87 Hz, 1H), 1.66 (s, 3H), 1.25 (s, 3H). NH$_2$ was not clear. $^{19}$F NMR (376 MHz, Chloroform-d) δ -110.82 (br. s., 1F), -125.57 (d, J=39.88 Hz, 1F). Relative stereochemsitry was confirmed by 2D NMR in a method analog to Example 110.

Example 115: (4S,6S)-2-amino-N-(2,2-difluoroethyl)-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazine-6-carboxamide

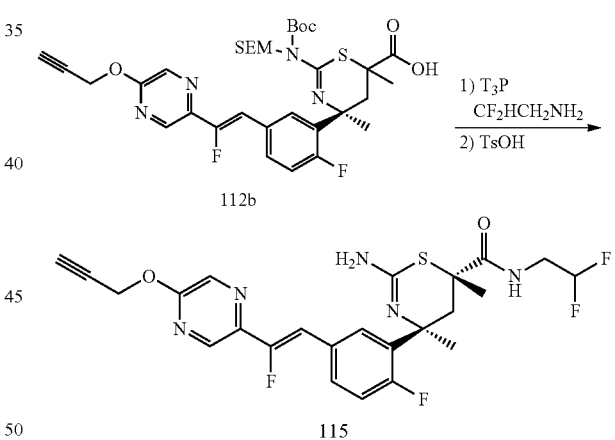

This compound (13 mg, 34% overall yield) as a white solid was prepared in a fashion similar to that described for Example 113, here starting from 2,2-difluoroethylamine (Matrix Scientific) (30 mg, 0.366 mmol) and acid 112b (50 mg, 0.073 mmol). MS (ESI +ve ion) m/z: [M+1]=522. $^1$H NMR (400 MHz, Chloroform-d) δ 8.38 (s, 1H), 8.26 (s, 1H), 7.77 (dd, J 1.86, 7.92 Hz, 1H), 7.57-7.65 (m, 1H), 7.26-7.30 (m, 1H), 7.05 (dd, J=8.41, 11.74 Hz, 1H), 6.76-6.91 (m, 1H), 5.69-6.07 (m, 1H), 4.94-5.10 (m, 2H), 5.03 (d, J 2.35 Hz, 2H), 3.55-3.76 (m, 2H), 3.08 (d, J=14.09 Hz, 1H), 2.53 (t, J=2.35 Hz, 1H), 1.71 (d, J 14.09 Hz, 1H), 1.51 (s, 3H), 1.49 (s, 3H). $^{19}$F NMR (376 MHz, Chloroform-d) δ -111.09 (br. s., 1F), -123.18--122.72 (m, 1F), -125.83 (d, J=39.88 Hz, 1F). Relative stereochemistry was confirmed by 2D NMR in a method analog to Example 110.

Example 116: (4S,6S)-2-amino-4-(5-((Z)-2-(5-cyanopyridin-2-yl)-2-fluorovinyl)-2-fluorophenyl)-N,4,6-trimethyl-5,6-dihydro-4H-1,3-thiazine-6-carboxamide

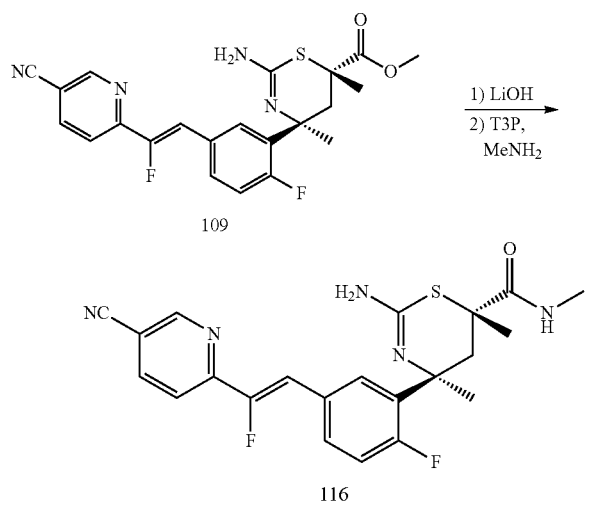

This compound was prepared in a 2-step protocol similar to that described for Example 111, here starting from ester 109. MS (ESI +ve ion) m/z: [M+1]=442. $^1$H NMR (400 MHz, DMSO-d$_6$) δ 9.07 (s, 1H), 8.44 (dd, J 2.05, 8.31 Hz, 1H), 7.96 (d, J 6.85 Hz, 1H), 7.85 (d, J=8.22 Hz, 2H), 7.69 (br. s., 1H), 7.15-7.35 (m, 2H), 6.05 (br. s., 2H), 3.28 (s, 1H), 2.62 (d, J 4.50 Hz, 3H), 2.54 (d, J 4.69 Hz, 1H), 1.37 (s, 3H), 1.24 (s, 3H). $^{19}$F NMR (376 MHz, DMSO-d$_6$) δ −109.64 (br. s., 1F), −124.59 (d, J=39.88 Hz, 1F).

Biological Evaluation

Provided in this section is the biological evaluation of the specific examples provided herein. In particular, Table 2 contains biological activity data. The data presented in Table 2 provides the IC$_{50}$ (μM) for the specific examples obtained in a BACE1 enzyme assay, BACE1 cell assay, BACE2 enzyme assay and CatD assay.

TABLE 2

| Ex. No. | BACE1 Enzyme IC$_{50}$ (μM) | BACE1 Cell IC$_{50}$ (μM) | BACE2 Enzyme IC$_{50}$ (μM) | Cat D Enzyme IC$_{50}$ (μM) |
|---|---|---|---|---|
| 100 | 0.220 | 0.357 | 0.191 | 36.9 |
| 101 | 0.098 | 0.049 | 0.601 | 52.0 |
| 102 | 0.124 | 0.148 | 0.064 | 211.0 |
| 103 | 0.074 | 0.015 | 0.482 | 186.0 |
| 104 | 0.212 | 0.468 | 0.185 | 133.0 |
| 105 | 0.045 | 0.377 | 0.049 | 73.7 |
| 106 | 0.054 | 0.215 | 0.075 | 91.0 |
| 107 | 0.068 | 0.522 | 0.090 | 281.8 |
| 108 | 0.016 | 0.044 | 0.231 | 385.6 |
| 109 | 0.016 | 0.024 | 0.281 | 95.6 |
| 110 | 0.004 | 0.002 | 0.13 | 250.0 |
| 111 | 0.098 | 0.201 | 1.47 | 300.5 |
| 112 | 0.037 | 0.011 | 1.305 | 79.9 |
| 113 | 0.022 | 0.010 | 0.835 | 178.0 |
| 114 | 0.006 | 0.002 | 0.358 | 21.8 |
| 115 | 0.024 | 0.018 | 0.76 | 40.2 |
| 116 | 0.025 | 0.010 | 0.56 | 68.6 |

The results presented in Table 2 have been generated with the in vitro assays described below. These assays may be used to test any of the compounds described herein to assess and characterize a compound's ability to modulate BACE activity and to regulate the cleavage of Aβ precursor protein, thereby reducing or inhibiting the production of Aβ protein.

In Vitro Enzymatic BACE1 and BACE2 FRET (Fluorescence Resonance Energy Transfer) Assays The cDNAs for both human recombinant BACE1 and 2 with C-terminal 6-His Tags were cloned into transient protein expression vectors, which were subsequently transfected into mammalian cell lines. These recombinant proteins were further purified using Ni-NTA affinity chromatography (Qiagen). The assay buffer used in these screens was 0.05 M acetate, pH 4.5, 8% DMSO final, 100 μM genapol (which is a nonionic detergent, below its Critical Micelle Concentration). The β-secretase enzyme (0.02 nM for BACE1 and 0.64 nM for BACE2), which was pre-incubated for one hour with the test compound, typically in about 1uL of DMSO according to a serial dilution, was added thereto. The assay was effectively started by the addition of FRET substrate (50 nM) and the combination was incubated for one hour. The FRET assay was terminated by the addition of tris buffer, which raised the pH to neutrality, and the fluorescence was determined. The FRET substrate was a peptide with commercially available fluorophore and quencher, on opposite sides of the BACE cleavage site. The specific FRET substrate used in this assay was made by Amgen in-house. Commercially available FRET substrates, for example, the FRET substrate offered with the BACE1 FRET Assay Kit sold by ThermoFisher Scientific (Catalog Number P2985), may be used in this assay with the appropriate modifications, which are within the purview of the ability of a person with ordinary skill in the art. Proteolytic cleavage of the FRET substrate released quenching of fluorescence (excitation 488 nm and emission 590 nm).

The in vitro BACE FRET enzyme data for each of the Examples is provided in Table 2.

In Vitro BACE1 Cell-Based Assay

The cell-based assay measures inhibition or reduction of Aβ40 in conditioned medium of test compound treated cells expressing amyloid precursor protein. Cells stably expressing Amyloid Precursor Protein (APP) were plated at a density of 45K cells/well in 384 well plates (Corning/BioCoat 354663). The test compounds were then added to cells in 22-point dose response concentrations with the starting concentration being 62.5 μM. The compounds were diluted from stock solutions in DMSO and the final DMSO concentration of the test compounds on cells was 0.625%. The cells were cultivated overnight at 37° C. and 5% CO$_2$ in DMEM supplemented with 10% FBS. After 24 h of incubation with the test compounds, the conditioned media was collected and the Aβ40 levels were determined using HTRF (Homogeneous Time Resolved Fluorescence). The IC$_{50}$ of the compound was calculated from the percent of control or percent inhibition of Aβ 40 as a function of the concentration of the test compound.

The HTRF to detect Aβ40 was performed in 384 well plates (Costar 3658). The antibody pair that were used to detect Aβ 40 from cell supernatants were ConfAb40 antibody (Amgen in-house) and biotinylated 6E10 (BIOLEGEND). As an alternative to ConfAb40, a commercially available antibody, Anti-beta Amyloid 1-40 antibody [BDI350] from Abcam, Cambridge, Mass. 02139-1517 (Product code: ab20068), may be used in this assay. The concentrations were 0.35 μg/mL of ConfAb40 antibody and 1.33 µg/mL of 6E10-biotinylated antibody, as well as 4.5 µg/mL of Streptavidin Allophycocyanin Conjugate (ThermoFisher Scientific) in HTRF Buffer (1M Hepes pH 7.5, 1M NaCL, 1% BSA, 0.5% Tween 20).

The conditioned media was incubated with above antibodies and Streptavidin Allophycocyanin Conjugate for 30-60 minutes at 23° C. The final readout was performed on Envision from PerkinElmer.

The in vitro BACE cell-based data for each of the Examples is provided in Table 2.

In Vitro Enzymatic Cathepsin D (CatD) FRET Assay

Recombinant CatD was expressed in CHO cells. The assay buffer for CatD was 0.05 M citrate pH 3.5, 10% DMSO final, 5 mM CHAPS. The CatD enzyme (9 nM) was pre-incubated for one hour with inhibitors, typically in about 1uL of DMSO according to a serial dilution, is added thereto. The assays was effectively started by the addition of different FRET substrates (20 nM for CatD) and the combination was incubated for one hour. The FRET assay was terminated with by addition of tris buffer, which raises the pH to neutrality, and the fluorescence was determined. The FRET substrate was a peptide with commercially available fluorophore and quencher, on opposite sides of the CatD cleavage site. The CatD substrate peptide sequence was based on sequence #1 of Table 1 from Gulnik et al., *FEBS Lett.* 413(2):379-384 (1997). Proteolytic cleavage of the FRET substrate released quenching of fluorescence (CatD excitation 500 nm and emission 580 nm).

Alternatively, a CatD assay may also be run according to the procedure described in Yasuda et al., *J. Biochem.* 125 (6):1137-1143 (1999). In addition, the CatD and Cathepsin E assays are described in International Patent Application Publication No. WO2011069934.

The in vitro CatD FRET assay data for each of the Examples is provided in Table 2, conducted by the first procedure described above. As shown by the high micromolar CatD data (very poorly active or inactive against CatD), the compounds disclosed herein possess the unexpected property of little to no ability to inhibit the activity of CatD. Thus, with this surprising selectivity profile, the compounds provided herein are believed to minimize, reduce or completely eliminate any risk of retinal atrophy and abnormal development of the eye and of the retinal pigmented epithelium as it relates to the normal function and activity of CatD.

In Vivo Inhibition of β-Secretase

Several animal models, including mouse, rat, dog, and monkey, may be used to screen for inhibition of β-secretase activity in vivo following administration of a test compound. This procedure may be used to show that the compounds provided herein reduce the formation and/or deposition of Aβ peptide in the cerebrospinal fluid (CSF) as well as in the brain. Animals to be used in this experiment can be wild type, transgenic, or gene knockout animals. For example, the Tg2576 mouse model, prepared and conducted as described in Hsiao et al., *Science* 274:99-102 (1996), and other non-transgenic or gene knockout animals are useful to analyze in vivo inhibition of Aβ peptide production in the presence of test compounds.

Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of Aβ levels and test compound concentrations (Dovey et al., *J. Neurochem.*, 76(1):173-181 (2001)) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween 80. A separate group of animals receive 2% hydroxypropyl methylcellulose, 1% Tween 80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., *J. Pharmacol. Exp. Ther.* 313(2):902-908 (2005)), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Aβ by specific sandwich ELISA assays based on ECL (Electrochemiluminescence) technology. For example, rat Aβ40 is measured using biotinylated-4G8 (Signet) as a capture antibody and Fab40 (an in-house antibody specific to the C-terminal of Aβ40) as a detection antibody. For example, 4 hours after administration of 30 mg/kg oral dose of the test compound in 2% hydroxypropyl methylcellulose, 1% Tween 80 (pH2.2) to 200 g male Sprague Dawley rats, Aβ peptide levels are measured for reduction by X % and Y % in cerebrospinal fluid and brain, respectively, when compared to the levels measured in the vehicle-treated or control mice. Alternatively, the antibody sold with the V-PLEX abeta40 Peptide (4G8) Kit, commercially available from Meso Scale Diagnostics (MSD), Rockville, Md. 20850-3173 (Catalog NO. K150SJE-1) may be used in this assay.

This procedure may be used to show that the compounds provided herein reduce the formation and/or deposition of Aβ peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs.

Methods of Use

According to the amyloid cascade hypothesis, cerebral deposition of amyloid-beta (Aβ) peptide is critical for Alzheimer's disease (AD) pathogenesis. Aβ peptide generation is initiated when β-secretase (BACE1) cleaves the amyloid precursor protein. De Meyer et al. re-affirm the putative role that the accumulation of Aβ peptide in cerebral spinal fluid (CSF) in a subject plays in the progression of symptoms, initially revealed as mild cognitive impairment, which ultimately leads to AD. *Arch Neurol.* 67(8):949-956 (2010). Aβ peptides generated from amyloid precursor protein (APP) by proteolytic cleavage, such as by aspartyl protease enzymes, including β-secretase (BACE) and γ-secretase, likely play a causal role in AD pathogenesis (Tanzi et al., *Cell* 120(4):545-555 (2005); Walsh et al., *Neuron* 44(1):181-193 (2004)). Although the precise mechanisms of Aβ toxicity are unclear, oligomeric forms of Aβ may contribute to cognitive decline by altering synaptic structure and function (Palop et al., *Nat. Neurosci.* 13(7): 812-818 (2010); Selkoe, *Behav. Brain Res.* 192(1):106-113 (2008); Shankar et al., *Nat. Med.* 14(8):837-842 (2008)). Transgenic mouse models that overexpress mutant APP and produce high levels of Aβ show amyloid plaque deposition, synaptic deficits, learning and memory impairments, and other behavioral abnormalities (Games et al., *Nature* 373: 523-527 (1995); Gotz et al., *Mol. Psychiatry* 9(7):664-683 (2004); Hsia et al., *Proc. Natl. Academy of Science USA* (96): 3228-3233, 1999; Hsiao et al., *Science* (274): 99-102, 1996, citing Harris et al, *Neuron* (68): 428-441, 2010).

For many years now, BACE1 has been a prime target for designing drugs to prevent or treat AD. Vassar et al., *Lancet Neurol.* 13:319-329 (2014). Several pharmaceutical companies are presently pursuing BACE1 inhibitors in human clinical trials. Id. at abstract.

For example, MK-8931, a small molecule inhibitor of BACE1, was the first molecule to enter phase I clinical trials. *Yan, Transl. Neurodegener.* 5(13):1-11 (2016) at page 4. MK-8931 was shown to have an excellent safety profile with no immediately noticeable side effects. Id. Merck was able to show that MK-8931 enters the brain and blocks β-secretase by showing that MK-8931 significantly reduced CSF Aβ peptide concentrations in a sustained and dose-dependent manner. Vassar et al., *Lancet Neurol.* 13:319-329 (2014) at page 323. MK-8931 is currently evaluated in a phase II/III clinical trial to assess the efficacy and safety of the compound for the treatment of AD patients with amnestic mild cognitive impairment (prodromal AD). *Yan, Transl. Neurodegener.* 5(13):1-11 (2016) at page 4.

Further, E2609, a BACE inhibitor identified by Eisai, showed significant reduction in Aβ peptide levels in the CSF and plasma in nonhuman primates. *Yan, Transl. Neurodegener.* 5(13):1-11 (2016) at page 7. E2609 did not show clinical significant safety concerns after repeated doses up to 200 mg in a phase I clinical trial. Id. After 14d dosing the Aβ peptide level reduction in the CSF was statistically significant compared to baseline (46.2% (25 mg), 61.9% (50 mg), 73.8% (100 mg), 79.9% (200 mg)). Id. In November 2014, Eisai stated that a phase II dose-finding study in patients with mild cognitive impairment (MCI) due to AD or prodromal AD and a positive amyloid PET-scan will be conducted in collaboration with Biogen.

Additionally, companies are also developing therapies targeting asymptomatic patients. JNJ-54861911, which was first developed by Shionogi & Co. in Japan and later in collaboration with Janssen, demonstrated an ability to cross the blood-brain barrier and to dose-dependently reduce Aβ peptide concentrations. *Yan, Transl. Neurodegener.* 5(13):1-11 (2016) at pages 5-7. For example, an oral dose of 95 mg once daily achieved Aβ peptide reduction of up to 95% in CSF. Id. In October 2015, Janssen and Shionogi launched a phase trial targeting asymptomatic subjects that are at risk for developing Alzheimer's dementia. Id.

Similarly, Amgen and Novartis announced in late 2015 a collaboration to co-develop Novartis' BACE inhibitor CNP520. *Yan, Transl. Neurodegener.* 5(13):1-11 (2016) at page 8. The study is aimed at, inter alia, showing that CNP520 "can slow down the onset and progression of clinical symptoms associated with Alzheimer's disease (AD) in participants at the risk to develop clinical symptoms based on their age and genotype." https://clinicaltrials.gov/ct2/show/NCT02565511 (last visited Oct. 23, 2016).

The compounds disclosed herein have been shown to modulate, and specifically inhibit the activity of the β-secretase enzymes as shown in Table 2 for specific examples disclosed herein, thereby reducing the generation of Aβ peptide. Accordingly, the compounds provided herein are useful for, for example, the prevention or treatment of β-secretase related diseases, including, but not limited to, AD. The compounds provided herein have the ability to modulate the activity of the β-secretase enzyme, thereby regulating the production of Aβ peptide and reducing the formation and deposition of Aβ peptide in both the cerebral spinal fluid as well as in the brain, resulting in a decrease of Aβ plaque in the brain.

More specifically, provided are the following uses for the compounds disclosed herein:

Provided are the compounds disclosed herein for use in reducing beta amyloid peptide levels in the cerebral spinal fluid of a subject.

Provided are the compounds disclosed herein for use in treating AD, cognitive impairment, or a combination thereof in a subject. In one embodiment, the compounds provided herein are useful for treating various stages and degrees of AD, including without limitation, mild, moderate and severe AD. In another embodiment, the compounds provided herein are useful for treating preclinical AD, mild cognitive impairment (MCI) due to AD, and dementia due to AD. In yet another embodiment, the compounds provided herein may be used to treat prodromal subjects.

Provided are the compounds disclosed herein for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of AD, or a combination thereof in a subject.

Provided are the compounds disclosed herein for use in reducing formation of plaque in the brain of a subject.

As previously discussed, in certain embodiments, the compounds described herein are to be understood to include all stereoisomers, tautomers, isotopically-labelled forms thereof or pharmaceutically acceptable salts of any of the foregoing or solvates of any of the foregoing or amorphous and crystalline forms (polymorphs) of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Dosage, Formulation, and Route of Administration

The amount of compound(s) which is/are administered and the dosage regimen for treating neurological disorders and β-secretase mediated diseases with the compounds and/or compositions disclosed herein depends on a variety of factors, including the age, weight, sex and medical condition of the subject, the type of disease, the severity of the disease, the route and frequency of administration, and the particular compound employed. A daily dose of about 0.01 to 500 mg/kg, or in some embodiments, between about 0.01 and about 50 mg/kg, and in still other embodiments between about 0.01 and about 30 mg/kg body weight may be appropriate. In yet other embodiments, a daily dose of between about 0.1 and about 10 mg/kg body weight may be appropriate and should be useful for all uses disclosed herein. The daily dose can be administered a number of times a day such as from one to four doses per day.

While it may be possible to administer a compound disclosed herein alone in the uses described, the compound administered normally will be present as an active ingredient in a pharmaceutical composition. Thus, in another embodiment, provided herein is a pharmaceutical composition comprising a compound disclosed herein in combination with a pharmaceutically acceptable excipient, such as diluents, carriers, adjuvants and the like, and, if desired, other active ingredients. In one embodiment, a pharmaceutical composition may comprise a therapeutically effective amount of a compound disclosed herein.

The compound(s) disclosed herein may be administered by any suitable route in the form of a pharmaceutical composition adapted to such a route and in a dose effective for the treatment intended. The compounds and compositions present herein may, for example, be administered orally, mucosally, topically, rectally, pulmonarily, such as by inhalation spray, or parentally including intravascularly, intravenously, intraperitoneally, subcutaneously, intramuscularly, intrasternally, and by infusion techniques, in dosage unit formulations containing conventional pharmaceutically acceptable excipients such as carriers, adjuvants, and vehicles.

For oral administration, the pharmaceutical composition may be in the form of, for example, a tablet, capsule, suspension or liquid. The pharmaceutical composition is typically made in the form of a dosage unit containing a particular amount of the active ingredient. Examples of such dosage units are tablets or capsules. For example, these may contain an amount of active ingredient from about 1 to 2000 mg, from about 1 to 500 mg, and from about 5 to 150 mg.

For therapeutic purposes, the compounds provided herein are ordinarily combined with one or more diluents or other "excipients" appropriate to the indicated route of administration.

If orally administered on a per dose basis, the compounds provided herein may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other excipients and modes of administration are well and widely known in the pharmaceutical art. The active ingredient may also be administered by injection as a composition with suitable excipients including saline, dextrose, or water, and optionally comprising one or more of a cosolvent such as propylene glycol or emulsifier such as, for example, Tween 80. Such formulations may also include compounds such as a cyclodextrin (for example, Captisol).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and in some embodiments may be from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional excipients, such as preservatives, stabilizers, wetting agents, emulsifiers, buffers etc. Tablets and pills can additionally be prepared with enteric coatings. Such compositions may also comprise excipients, such as wetting, sweetening, flavoring, and perfuming agents. Accordingly, in yet another embodiment of the present disclosure, there is provided a method of manufacturing a medicament, the method comprising combining an amount of a compound according to Formula I with a pharmaceutically acceptable diluent to manufacture the medicament.

In yet another embodiment, the provided herein is a method of manufacturing a medicament for the treatment of AD, the method comprising combining an amount of a compound provided herein with a pharmaceutically acceptable excipient to manufacture the medicament.

COMBINATIONS

While the compounds disclosed herein can be dosed or administered as the sole active pharmaceutical agent, they can also be used in combination with one or more compounds provided herein or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound provided herein and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds provided herein may be in conjunction with additional therapies known to those skilled in the art in the prevention or treatment of β-secretase, γ-secretase and/or other reagents known in influence the formation and/or deposition of Aβ peptide, otherwise responsible for the formation of plaque in the brain.

If formulated as a fixed dose, such combination products employ the compounds disclosed herein within the accepted dosage ranges. The compounds provided herein may also be administered sequentially with other known medicinal agents. This disclosure is not limited in the sequence of administration; compounds provided herein may be administered either prior to, simultaneous with or after administration of the known anti-inflammatory agent.

The foregoing description is merely illustrative and is not intended to limit the disclosure to the described compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I

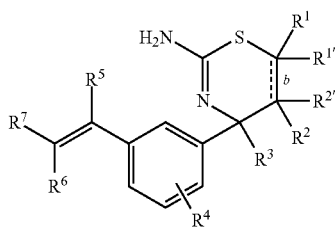

or a tautomer thereof, or a pharmaceutically acceptable salt of said compound or tautomer, wherein $R^1$ and $R^{1'}$, independently, are H, $C_{1-6}$alkyl, —C(O)O$C_{1-6}$alkyl, —C(O)NH$C_{1-6}$alkyl, or —C(O)-heterocycloalkyl, wherein the $C_{1-6}$alkyl and the $C_{1-6}$alkyl portions of —C(O)O$C_{1-6}$alkyl and —C(O)NH$C_{1-6}$alkyl are optionally substituted with one to three fluoro substituents;

$R^2$ and $R^{2'}$ are H;

b is a single bond, if $R^1$, $R^{1'}$, $R^2$ and $R^{2'}$ are present;

b is a double bond, if one of $R^1$ and $R^{1'}$ and one of $R^2$ and $R^{2'}$ is not present;

$R^3$ is $C_{1-4}$alkyl;

$R^4$ is halogen;

$R^5$ is H or F; and one of $R^6$ and $R^7$ is F or H and the other of $R^6$ and $R^7$ is a 6-membered nitrogen-containing heteroaryl, which heteroaryl is optionally substituted with halogen, —CN, or 2-propynyloxy, wherein at least one of $R^5$, $R^6$, or $R^7$ is F.

2. The compound according to claim 1, or a tautomer thereof, or a pharmaceutically acceptable salt of said compound or tautomer, wherein the compound of Formula I is a compound of Formula II

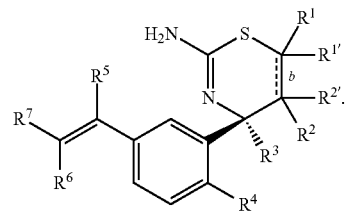

3. The compound according to claim 1, or a tautomer thereof, or a pharmaceutically acceptable salt of said compound or tautomer, wherein the compound of Formula I is a compound of Formula IIIA

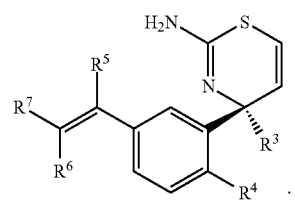

4. The compound according to claim 1, or a tautomer thereof, or a pharmaceutically acceptable salt of said compound or tautomer, wherein the compound of Formula I is a compound of Formula IIIB

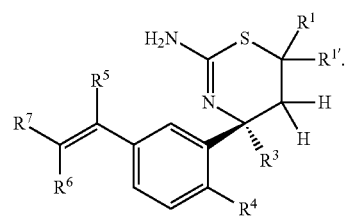

5. The compound according to claim 1, or a tautomer thereof, or a pharmaceutically acceptable salt of said compound or tautomer, wherein
$R^1$ is H,

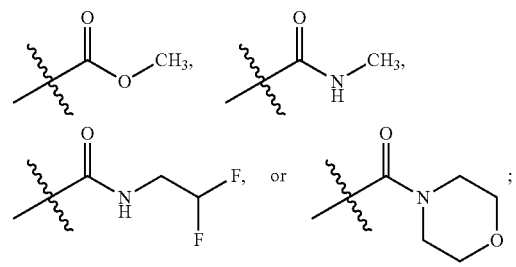

and
$R^{1'}$ is H or methyl.

6. The compound according to claim 1, or a tautomer thereof, or a pharmaceutically acceptable salt of said compound or tautomer, wherein $R^3$ is methyl.

7. The compound according to claim 1, or a tautomer thereof, or a pharmaceutically acceptable salt of said compound or tautomer, wherein $R^4$ is F.

8. The compound according to claim 1, or a tautomer thereof, or a pharmaceutically acceptable salt of said compound or tautomer, wherein $R^6$ and $R^7$ is F or H and the other of $R^6$ and $R^7$ is pyridyl or pyrazinyl, which pyridyl or pyrazinyl is optionally substituted with Cl, —CN, or 2-propynyloxy.

9. The compound according to claim 1, or a tautomer thereof, or a pharmaceutically acceptable salt of said compound or tautomer, wherein $R^6$ and $R^7$ is F or H and the other of $R^6$ and $R^7$ is pyridyl or pyrazinyl, which pyridyl or pyrazinyl is optionally substituted with —CN or 2-propynyloxy.

10. The compound according to claim 1, or a tautomer thereof, or a pharmaceutically acceptable salt of said compound or tautomer, wherein one of $R^6$ and $R^7$ is

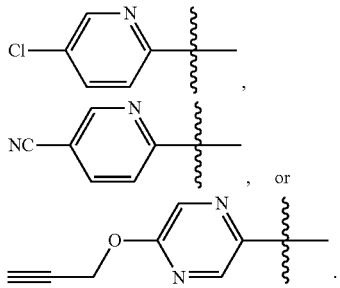

11. The compound according to claim 1, or a tautomer thereof, or a pharmaceutically acceptable salt of said compound or tautomer, wherein one of $R^6$ and $R^7$ is

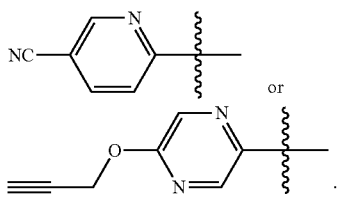

12. The compound according to claim 1, or a tautomer thereof, or a pharmaceutically acceptable salt of said compound or tautomer, wherein
$R^5$ is F and $R^6$ is H;
$R^5$ is F and $R^7$ is H; or
$R^5$ is H and $R^7$ is F.

13. The compound according to claim 1, or a tautomer thereof, or a pharmaceutically acceptable salt of said compound or tautomer, wherein
$R^5$ is H; and
$R^6$ is F.

14. The compound of claim 1, or a tautomer thereof, or a pharmaceutically acceptable salt of said compound or tautomer, selected from
(S,Z)-4-(5-(2-(5-chloropyridin-2-yl)-2-fluorovinyl)-2-fluorophenyl)-4-methyl-4H-1,3-thiazin-2-amine;
(S,Z)-6-(2-(3-(2-amino-4-methyl-4H-1,3-thiazin-4-yl)-4-fluorophenyl)-1-fluorovinyl)nicotinonitrile;
(S,Z)-4-(5-(2-(5-chloropyridin-2-yl)-2-fluorovinyl)-2-fluorophenyl)-4-methyl-5,6-dihydro-4H-1,3-thiazin-2-amine;
(S,Z)-6-(2-(3-(2-amino-4-methyl-5,6-dihydro-4H-1,3-thiazin-4-yl)-4-fluorophenyl)-1-fluorovinyl)nicotinonitrile;
(4S,6R)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate;
(4S,6S)-methyl 2-amino-4-(5-((Z)-2-(5-chloropyridin-2-yl)-2-fluorovinyl)-2-fluorophenyl)-4-methyl-5,6-dihydro-4H-1,3-thiazine-6-carboxylate;
(4S,6S)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate;
(4S,6R)-methyl 2-amino-4-(5-((Z)-2-(5-chloropyridin-2-yl)-2-fluorovinyl)-2-fluorophenyl)-4,6-dimethyl-5,6-dihydro-4H-1,3-thiazine-6-carboxylate;
(4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
(4S,6S)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
6-((Z)-2-(3-((4S,6S)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
(4S,6R)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
(4S,6S)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
((4S,6S)-2-amino-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazin-6-yl)(morpholino)methanone;
(4S,6S)-2-amino-N-(2,2-difluoroethyl)-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazine-6-carboxamide; or
(4S,6S)-2-amino-4-(5-((Z)-2-(5-cyanopyridin-2-yl)-2-fluorovinyl)-2-fluorophenyl)-N,4,6-trimethyl-5,6-dihydro-4H-1,3-thiazine-6-carboxamide.

15. The compound of claim 1, or a tautomer thereof, or a pharmaceutically acceptable salt of said compound or tautomer, selected from
(S,Z)-6-(2-(3-(2-amino-4-methyl-4H-1,3-thiazin-4-yl)-4-fluorophenyl)-1-fluorovinyl)nicotinonitrile;
(S,Z)-6-(2-(3-(2-amino-4-methyl-5,6-dihydro-4H-1,3-thiazin-4-yl)-4-fluorophenyl)-1-fluorovinyl)nicotinonitrile;
(4S,6R)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
(4S,6S)-methyl 2-amino-4-(5-((Z)-2-(5-cyanopyridin-2-yl)-2-fluorovinyl)-2-fluorophenyl)-4,6-dimethyl-5,6-dihydro-4H-1,3-thiazine-6-carboxylate;
6-((Z)-2-(3-((4S,6S)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
6-((Z)-2-(3-((4S,6R)-2-amino-4,6-dimethyl-6-(morpholine-4-carbonyl)-5,6-dihydro-4H-1,3-thiazin-4-yl)-4-fluorophenyl)-1-fluorovinyl)nicotinonitrile;
(4S,6R)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;
(4S,6S)-2-amino-4-(2-fluoro-5-((Z)-2-fluoro-2-(5-(2-propyn-1-yloxy)-2-pyrazinyl)ethenyl)phenyl)-N,4,6-trimethyl-5,6-dihydro-4H-1,3-thiazine-6-carboxamide;

((4S,6S)-2-amino-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazin-6-yl)(morpholino)methanone;

(4S,6S)-2-amino-N-(2,2-difluoroethyl)-4-(2-fluoro-5-((Z)-2-fluoro-2-(5-(prop-2-yn-1-yloxy)pyrazin-2-yl)vinyl)phenyl)-4,6-dimethyl-5,6-dihydro-4H-1,3-thiazine-6-carboxamide; or (4S,6S)-2-amino-4-(5-((Z)-2-(5-cyanopyridin-2-yl)-2-fluorovinyl)-2-fluorophenyl)-N,4,6-trimethyl-5,6-dihydro-4H-1,3-thiazine-6-carboxamide.

16. A pharmaceutical composition comprising the compound according to claim 1, or a tautomer thereof, or a pharmaceutically acceptable salt of said compound or tautomer, and a pharmaceutically acceptable excipient.

17. A method of reducing beta amyloid peptide levels in the cerebral spinal fluid of a subject in need thereof, the method comprising administering to the subject a therapeutically effective amount of the compound according to claim 1, or a tautomer thereof, or a pharmaceutically acceptable salt of said compound or tautomer.

18. A method of treating Alzheimer's disease, cognitive impairment or a combination thereof in a subject in need thereof, the method comprising administering to the subject a therapeutically effective amount of the compound according to claim 1, or a tautomer thereof, or a pharmaceutically acceptable salt of said compound or tautomer.

19. A method of treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject in need thereof, the method comprising administering to the subject a therapeutically effective amount of the compound according to claim 1, or a tautomer thereof, or a pharmaceutically acceptable salt of said compound or tautomer.

20. A method of reducing the formation of plaque in the brain of a subject in need thereof, the method comprising administering to the subject a therapeutically effective amount of the compound according to claim 1, or a tautomer thereof, or a pharmaceutically acceptable salt of said compound or tautomer.

* * * * *